US012576172B2

(12) United States Patent (10) Patent No.: US 12,576,172 B2

Callahan et al. (45) Date of Patent: Mar. 17, 2026

(54) ULTRAVIOLET LIGHT SANITIZING CART HAVING A WAND ASSEMBLY

(71) Applicant: THE BOEING COMPANY, Chicago, IL (US)

(72) Inventors: Kevin S. Callahan, Everett, WA (US); Jamie J. Childress, Mercer Island, WA (US)

(73) Assignee: The Boeing Company, Arlington, VA (US)

( * ) Notice: Subject to any disclaimer, the term of this patent is extended or adjusted under 35 U.S.C. 154(b) by 632 days.

(21) Appl. No.: 17/022,392

(22) Filed: Sep. 16, 2020

(65) Prior Publication Data

US 2021/0346541 A1 Nov. 11, 2021

Related U.S. Application Data

(60) Provisional application No. 63/055,592, filed on Jul. 23, 2020, provisional application No. 63/021,984, filed on May 8, 2020.

(51) Int. Cl.
 *A61L 2/10* (2006.01)
 *A61L 2/26* (2006.01)

(52) U.S. Cl.
 CPC .................. *A61L 2/10* (2013.01); *A61L 2/26* (2013.01); *A61L 2202/11* (2013.01); *A61L 2202/16* (2013.01); *A61L 2202/25* (2013.01)

(58) Field of Classification Search
 CPC ............................... A61L 2/10; A61L 2202/16
 See application file for complete search history.

(56) References Cited

U.S. PATENT DOCUMENTS

| | | | |
|---|---|---|---|
| 6,630,105 B1 | 10/2003 | O'Neill | |
| 9,095,633 B1 | 8/2015 | Dayton | |
| 2014/0059796 A1* | 3/2014 | Boodaghians | ......... B64D 11/00 |
| | | | 250/455.11 |
| 2019/0255201 A1* | 8/2019 | Rosen | ....................... A61L 2/10 |
| 2020/0085983 A1 | 3/2020 | Ramanand | |

FOREIGN PATENT DOCUMENTS

| | | |
|---|---|---|
| CN | 202554525 | 11/2012 |
| CN | 20152279 | 10/2016 |
| CN | 206007658 | 3/2017 |
| CN | 206910539 | 1/2018 |
| CN | 108904833 | 11/2018 |
| CN | 110038142 | 7/2019 |
| EP | 2772272 | 9/2014 |

(Continued)

OTHER PUBLICATIONS

KR 101142520 B1 _Translation.*

(Continued)

*Primary Examiner* — Elizabeth A Robinson
*Assistant Examiner* — Changru Chen
(74) *Attorney, Agent, or Firm* — Joseph M. Butscher; Carroll, Hoette & Butscher, LLC

(57) ABSTRACT

An ultraviolet (UV) light sanitizing cart including one or more first UV lamps configured to emit UV light, and one or more wand assemblies comprising one or more second UV lamps configured to emit UV light. The one or more wand assemblies are moveable between a stowed position and a deployed position.

24 Claims, 24 Drawing Sheets

(56) References Cited

FOREIGN PATENT DOCUMENTS

| | | | | |
|---|---|---|---|---|
| JP | H 03-218764 | 9/1991 | | |
| JP | 2014162474 | 9/2014 | | |
| KR | 200382161 | 4/2004 | | |
| KR | 200382161 Y1 * | 4/2005 | ............... | A61L 2/10 |
| KR | 101142520 B1 * | 5/2012 | ............... | A61L 2/10 |
| WO | 2016164362 | 10/2016 | | |
| WO | WO 2019/164810 | 8/2019 | | |
| WO | WO-2019170678 A1 * | 9/2019 | ............... | A61L 2/07 |

OTHER PUBLICATIONS

KR 200382161 Y1 _Translation.*
CN 108904833 A_Translation.*
WO 2019170678 A1_translation (Year: 2019).*
Extended European Search Report for EP 21165853.9-1104, dated Jan. 25, 2022.
U.S. Appl. No. 17/016,466, filed Sep. 10, 2020.
U.S. Appl. No. 29/735,235, filed May 19, 2020.
U.S. Appl. No. 17/039,011, filed Sep. 30, 2020.
U.S. Appl. No. 17/026,414, filed Sep. 21, 2020.
U.S. Appl. No. 17/020,942, filed Sep. 15, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/026,417, filed Sep. 21, 2020.
U.S. Appl. No. 17/020,951, filed Sep. 15, 2020.
"Honeywell UV Treatment System," https://aerospace.honeywell.com/en/learn/products/cabin/uv-cabin-system.
U.S. Appl. No. 17/026,435, filed Sep. 21, 2020.
Partial European Search Report for EP 21165853.9-1104, dated Oct. 5, 2021.
CN Office Action for CN App. No. 202110495947.4 sent Dec. 25, 2024 (and English translation).
CN Office Action for CN 202110495947.4, dated Oct. 17, 2024 (and English translation).

* cited by examiner

100

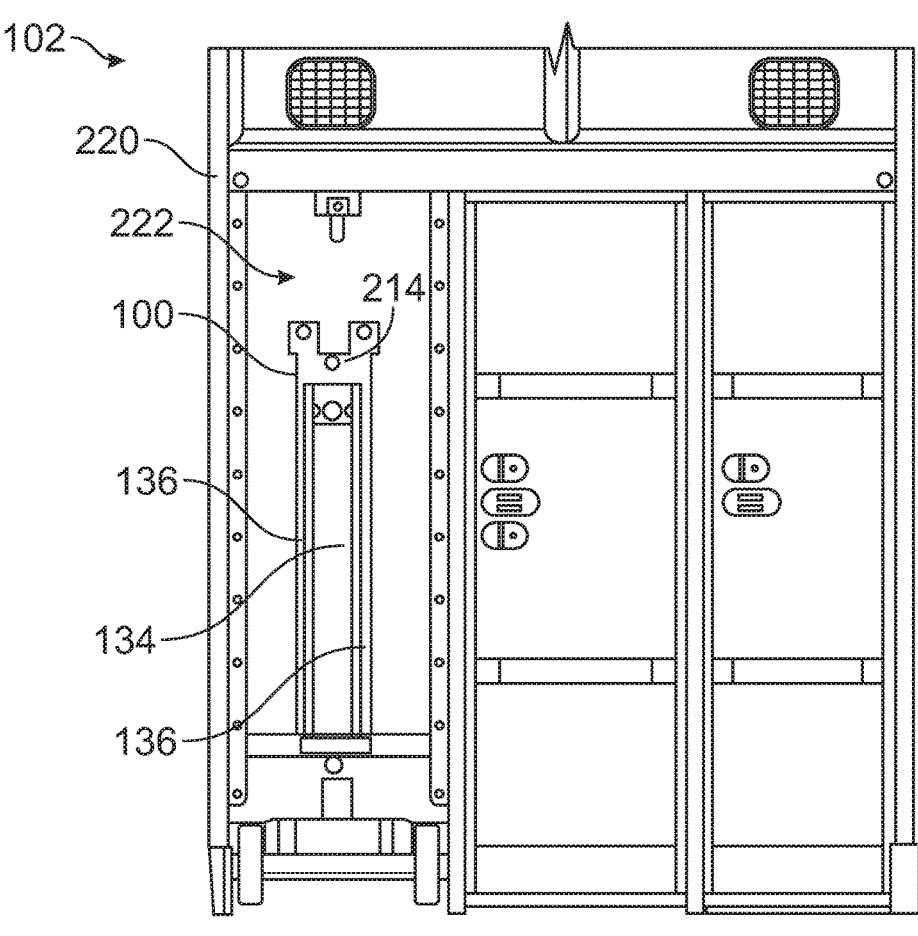
FIG. 7
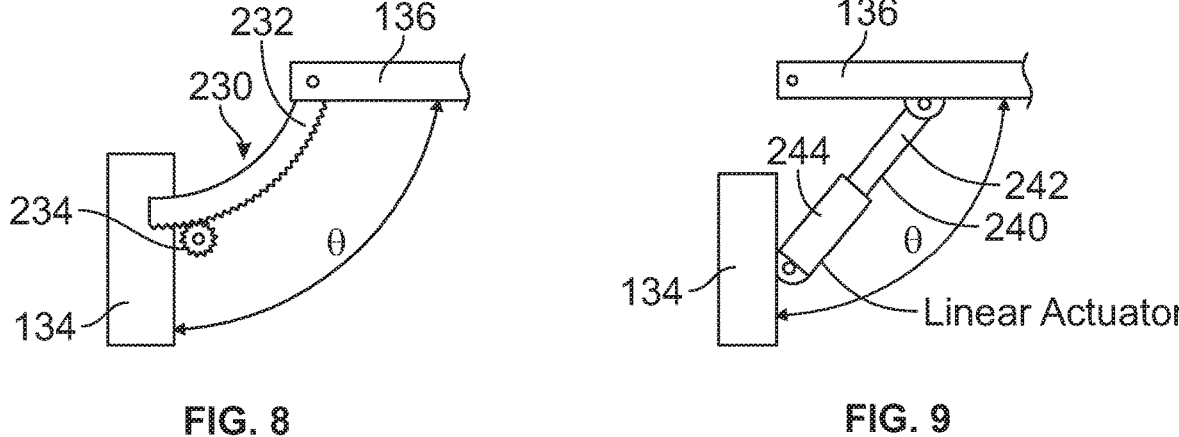
FIG. 8                    FIG. 9

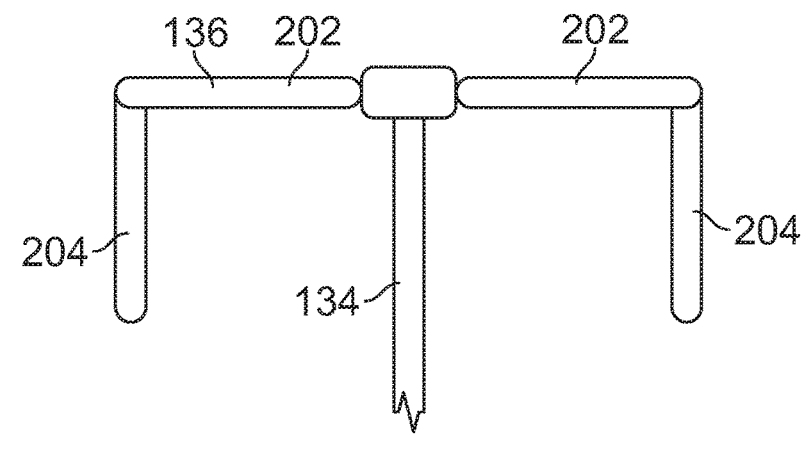
FIG. 14A
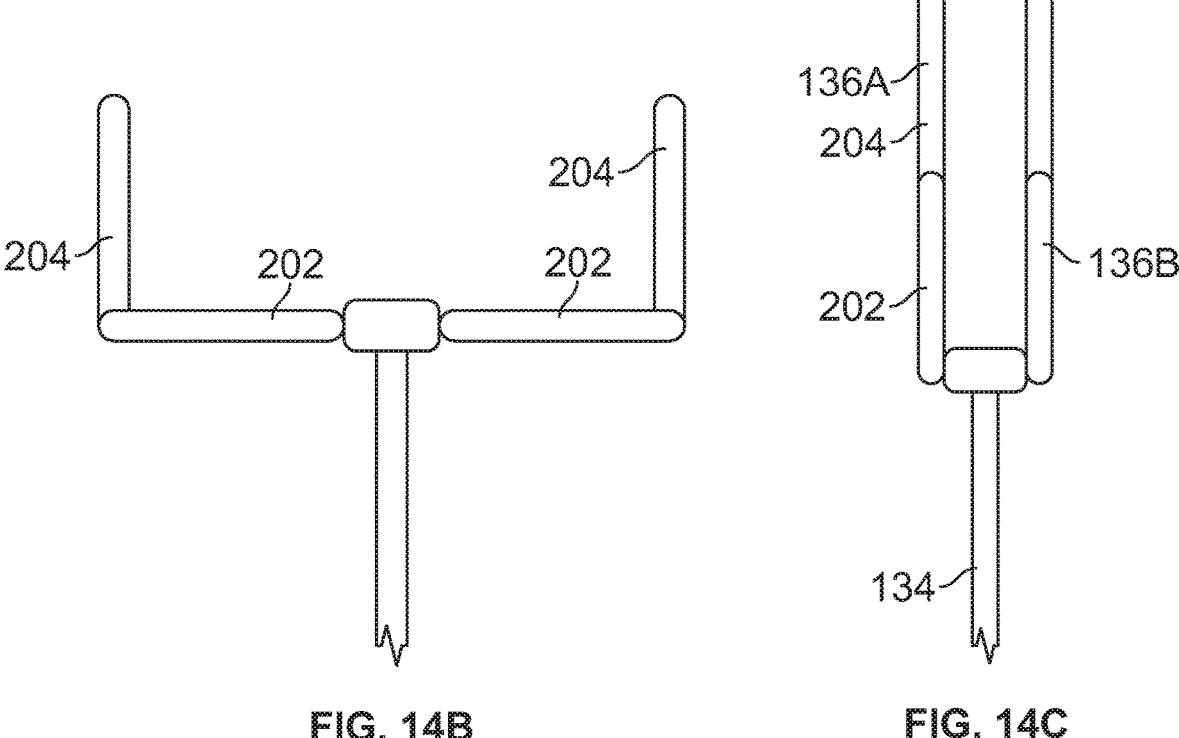
FIG. 14B   FIG. 14C

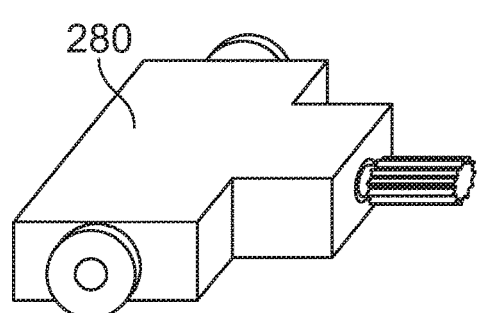
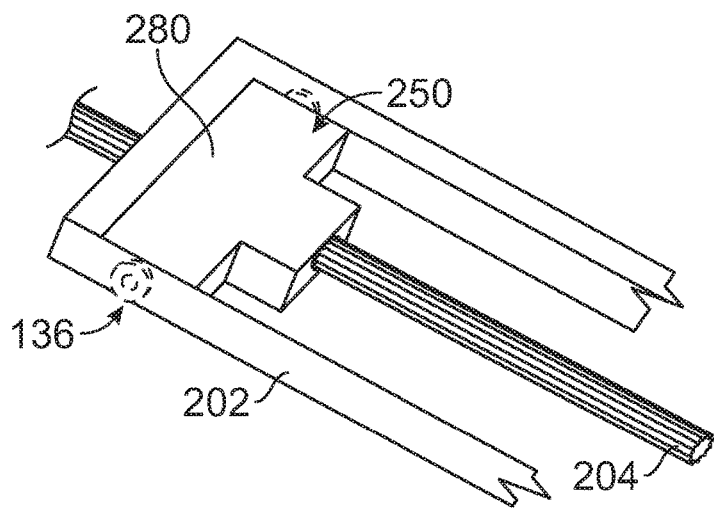
FIG. 15
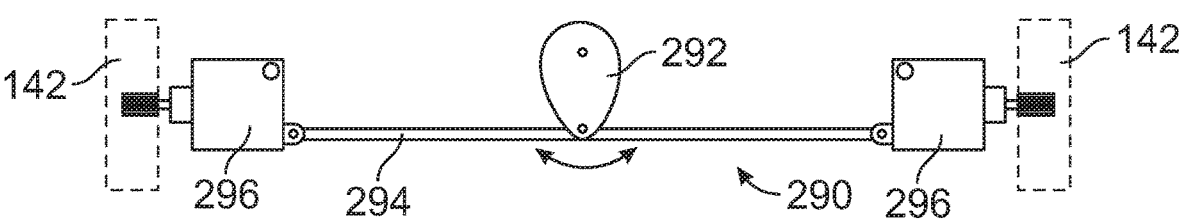
FIG. 16

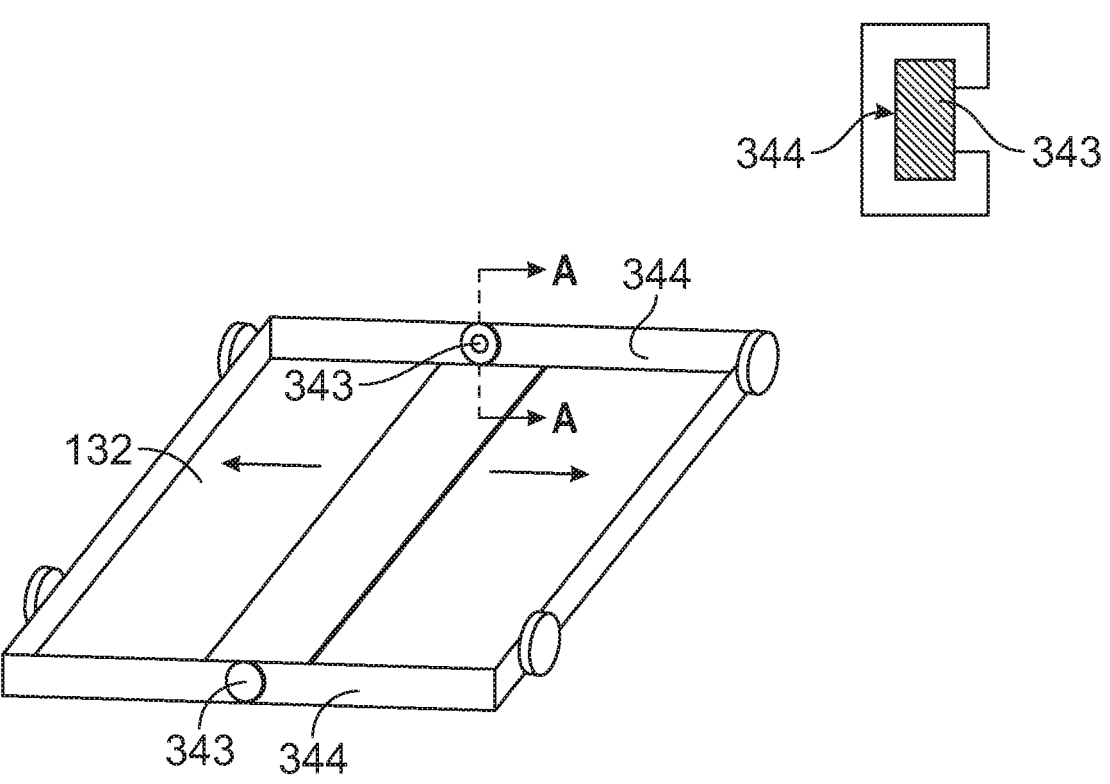
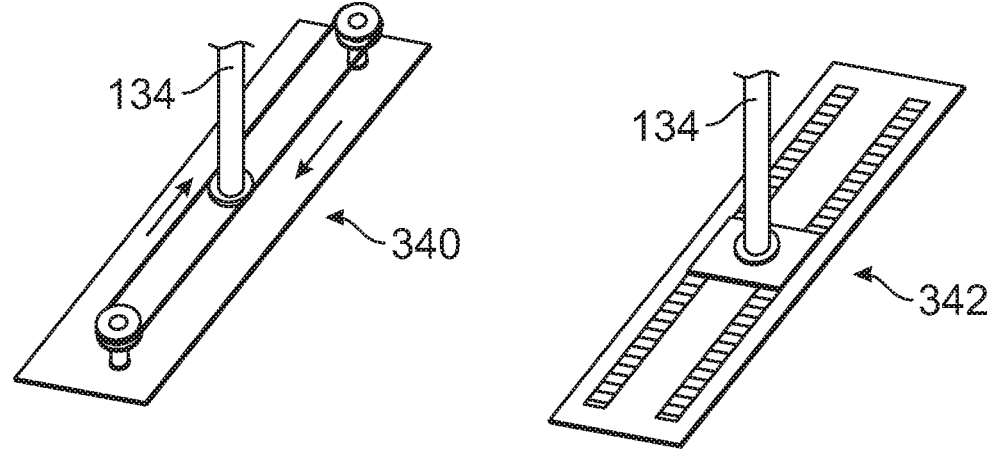
FIG. 22

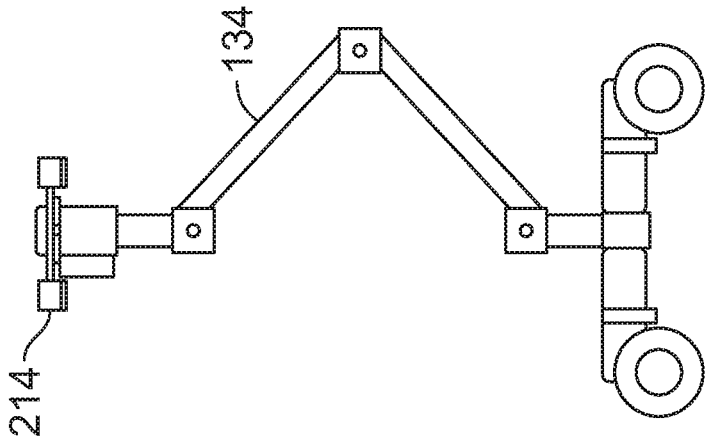
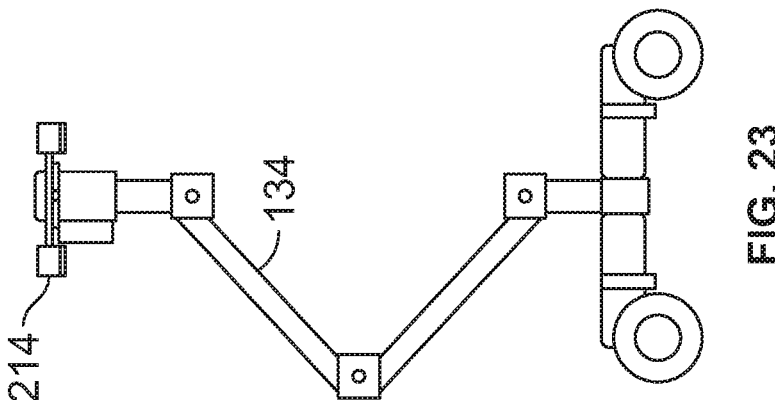
FIG. 23
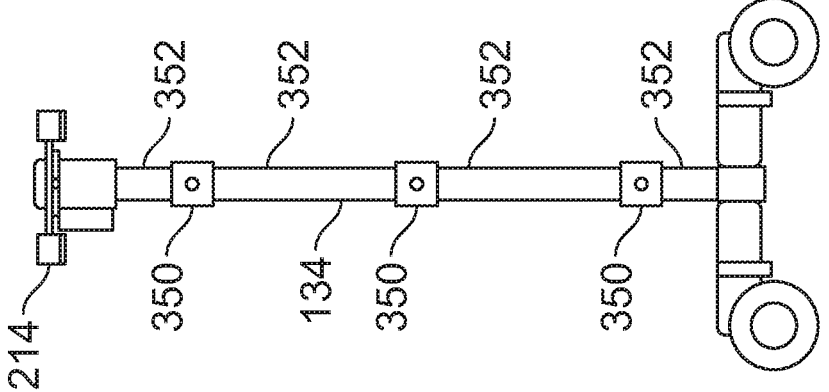

100

100

100

100

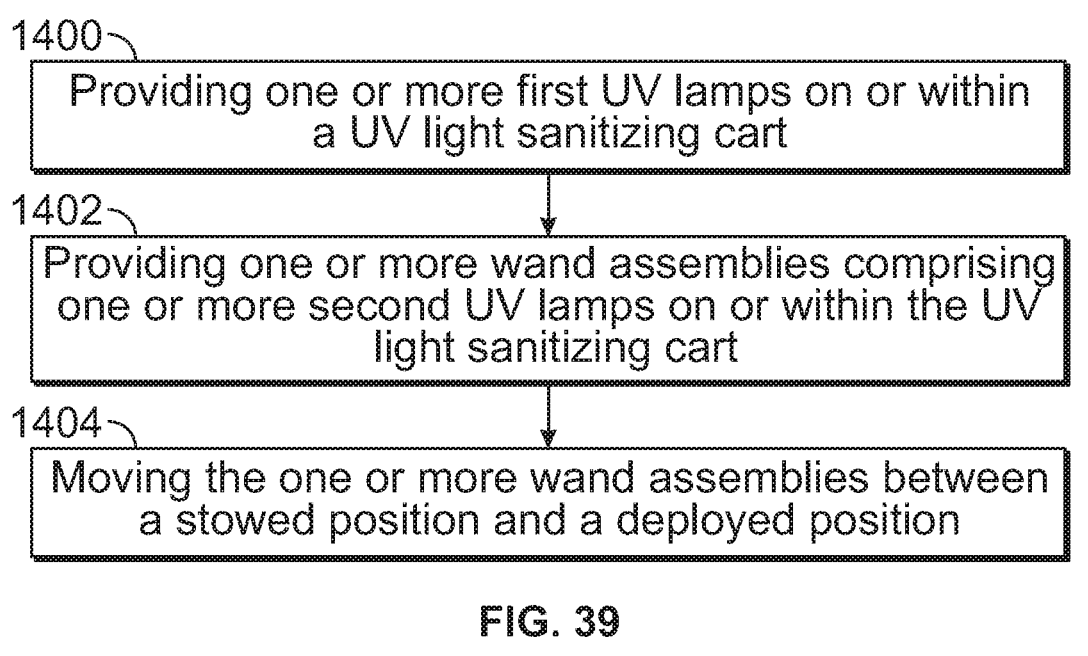

1400

Providing one or more first UV lamps on or within a UV light sanitizing cart

1402

Providing one or more wand assemblies comprising one or more second UV lamps on or within the UV light sanitizing cart

1404

Moving the one or more wand assemblies between a stowed position and a deployed position

FIG. 39

ULTRAVIOLET LIGHT SANITIZING CART HAVING A WAND ASSEMBLY

CROSS-REFERENCE TO RELATED APPLICATIONS

This application relates to and claims priority benefits from U.S. Provisional Patent Application No. 63/021,984, entitled "Portable Sanitizing Systems and Methods," filed May 8, 2020.

This application also relates to and claims priority benefits from U.S. Provisional Application No. 63/055,592, entitled "Ultraviolet Light Sanitizing Cart," filed Jul. 23, 2020.

FIELD OF THE DISCLOSURE

Examples of the subject disclosure generally relate to sanitizing equipment, such as may be used to sanitize structures and areas within vehicles, such as commercial aircraft, and more particularly to mobile equipment for autonomously or semi-autonomously sanitizing structures and areas using ultraviolet (UV) light.

BACKGROUND OF THE DISCLOSURE

Vehicles such as commercial aircraft are used to transport passengers between various locations. Systems are currently being developed to disinfect or otherwise sanitize surfaces within aircraft, for example, that use UV light. In order to sanitize a surface of a structure, a known UV light steriliization method emits a broad spectrum UVC light onto the structure.

Portable sanitizing systems having wand assemblies are being developed to sanitize components. A wand assembly of a portable sanitizing system includes a UV lamp that is configured to emit UV light. Typically, an operator moves the wand assembly over a surface of a component to sanitize the surface. However, the individual typically does not know if the wand assembly is being moved too fast or too slow to effectively and efficiently sanitize the surface. In general, manual processes for disinfecting surfaces using handheld devices have varying degrees of consistency.

Mobile sanitizing equipment is being developed that can roll or otherwise move along a path, such as an aisle of an internal cabin within an aircraft, and emit UV light onto structural surfaces as the equipment moves. However, known mobile sanitizing equipment has limited disinfecting effectiveness and consistency because the UV lights are suspended at a fixed height relative to the structures that are illuminated by the UV light as the equipment moves along the path. The result is that the UV lights may be located relatively far from the structural surfaces, and the distances between the UV lights and the structural surfaces can vary. The amount of disinfection or sanitization on a target surface is referred to as dosage, and is affected by the power of the UV light, the range or distance from the UV light source to the target surface, and the time of exposure. The speed of the equipment relative to the target surface affects the time of exposure. Due to the varying distances from the fixed UV light sources to different surfaces, the dosages applied to the different surfaces varies, resulting in inconsistent sanitization. Furthermore, the relatively far distances from the UV light sources to some of the surfaces and the lack of an ability to aim the UV light to surfaces may result in insufficient dosages of UV light applied to the surfaces. One method to increase the dosage for achieving a desirable amount of disinfection is to significantly slow the speed of the mobile sanitizing equipment to increase the time of exposure, but that makes the sanitizing process less efficient.

SUMMARY OF THE DISCLOSURE

A need exists for autonomous or semi-autonomous mobile UV sanitizing equipment that can consistently and efficiently disinfect structures and areas as the equipment moves.

With that need in mind, certain examples of the subject disclosure provide an ultraviolet (UV) light sanitizing cart including one or more first UV lamps configured to emit UV light, and one or more wand assemblies comprising one or more second UV lamps configured to emit UV light. The one or more wand assemblies are moveable between a stowed position and a deployed position.

In at least one example, the UV light sanitizing cart further includes a body having a mobile base. The one or more first UV lamps are secured to one or more portions of the body. As a further example, the one or more wand assemblies are connected to the body through one or more tethers. The one or more tethers can include one or more of a power cord, a cable, or an air hose.

In at least one example, the UV light sanitizing cart is a galley cart configured to be moved into and out of a compartment within a galley of an internal cabin of a vehicle.

In at least one example, the one or more first UV lamps and the one or more second UV lamps are configured to emit the UV light at a wavelength within the far UV spectrum. For example, the one or more first UV lamps and the one or more second UV lamps are configured to emit the UV light at a wavelength of 222 nm.

In at least one other example, the one or more first UV lamps and the one or more second UV lamps are configured to emit the UV light at a wavelength within the UVC spectrum. For example, the one or more first UV lamps and the one or more second UV lamps are configured to emit the UV light at a wavelength of 254 nm.

In at least one example, the one or more wand assemblies include a first wand assembly and a second wand assembly.

In at least one example, the one or more wand assemblies include a handle, and a sanitizing head coupled to the handle. The sanitizing head includes the one or more second UV lamps. As a further example, the sanitizing head is moveably coupled to the handle.

Certain examples of the subject disclosure provide an ultraviolet (UV) light sanitizing method including providing one or more first UV lamps on or within a UV light sanitizing cart; providing one or more wand assemblies comprising one or more second UV lamps on or within the UV light sanitizing cart; and moving the one or more wand assemblies between a stowed position and a deployed position.

BRIEF DESCRIPTION OF THE DRAWINGS

FIG. 7 is a view of the UV light sanitizing cart stowed within a monument within the internal cabin, according to an example of the subject disclosure.

FIG. 8 shows a curved rack and pinion actuator for raising and lowering the arms, and therefore the UV light array, of the UV light sanitizing cart, according to an example of the subject disclosure.

FIG. 9 shows a linear actuator for raising and lowering the arms, and therefore the UV light array, of the UV light sanitizing cart, according to an example of the subject disclosure.

FIGS. 14A-E depict various postures of the arms of the UV light sanitizing cart relative to a trunk thereof according to another example in which the outer members of the arms can pivot relative to the inner members.

FIG. 15 depicts an outer array carrier that is mounted to the inner member of an arm of the UV light sanitizing cart according to an example of the subject disclosure.

FIG. 16 depicts a steering mechanism for controlling the position of wheels of the UV light sanitizing cart, according to an example of the subject disclosure.

FIG. 22 depicts a base of the UV light sanitizing cart, according to an alternative example of the subject disclosure.

FIG. 23 depicts the trunk of the UV light sanitizing cart according to an alternative example of the subject disclosure.

FIG. 39 illustrates a flow chart of a UV light sanitizing method, according to an example of the subject disclosure.

DETAILED DESCRIPTION OF THE DISCLOSURE

Figure 1:
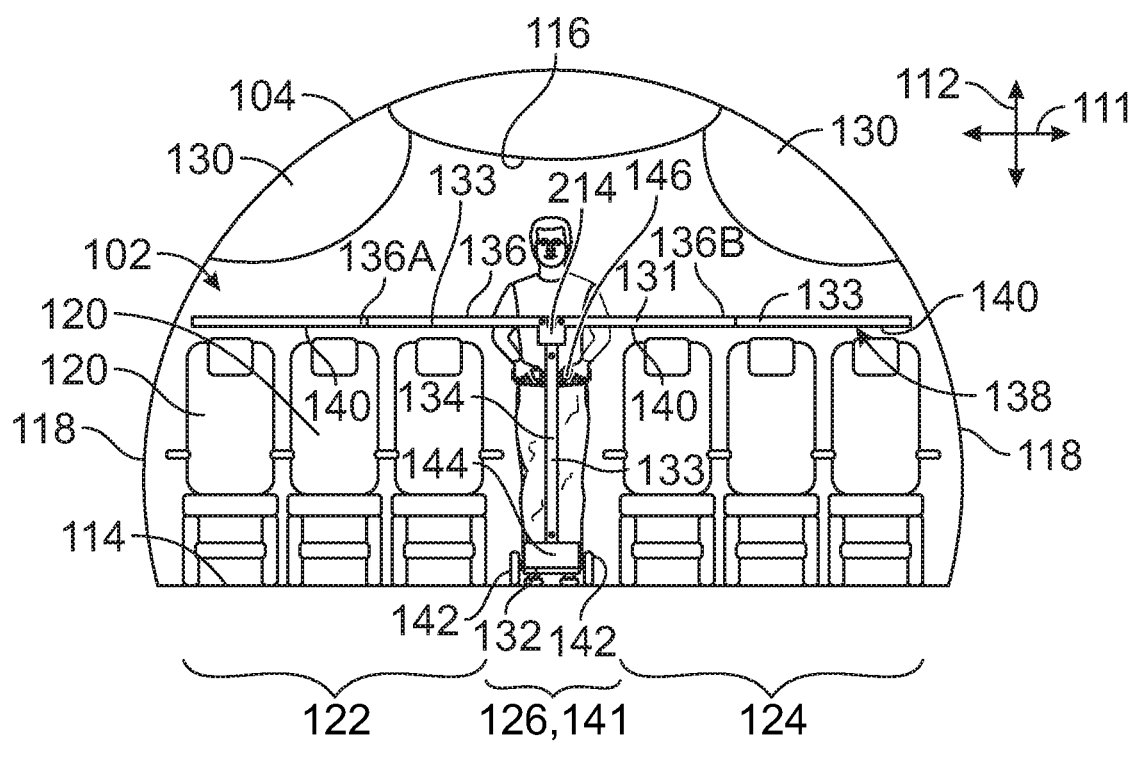
FIG. 1 is a rear or aft-facing view of an internal cabin of a vehicle including a UV light sanitizing cart, according to an example of the subject disclosure.

The foregoing summary, as well as the following detailed description of certain examples will be better understood when read in conjunction with the appended drawings. As used herein, an element or step recited in the singular and preceded by the word "a" or "an" should be understood as not necessarily excluding the plural of the elements or steps. Further, references to "one example" are not intended to be interpreted as excluding the existence of additional examples that also incorporate the recited features. Moreover, unless explicitly stated to the contrary, examples "comprising" or "having" an element or a plurality of elements having a particular condition can include additional elements not having that condition.

Certain examples of the subject disclosure provide an ultraviolet (UV) light sanitizing cart that emits UV light as the cart moves within an area. The cart includes an array of UV light sources that emit UV light. The UV light sources, or lamps as referred to herein, can emit light in a far UV light spectrum at one or more wavelengths that neutralize (e.g., kill) microbes. The microbes as referred to herein can include viruses and bacteria. The wavelengths of UV light emitted by the UV lamps may pose no risk to humans upon contact, such as 222 nm. The UV lamps may be excimer lamps. Optionally, the UV light sources can emit UV light at other wavelengths, such as within the UVC spectrum.

In at least one example, a wand assembly including an additional UV light source is coupled to the UV light sanitizing cart. The wand assembly is moveable between a stowed position on or within the cart, and a deployed position, in which the wand assembly is able to reach areas that the cart may not otherwise be able to reach.

The UV light sanitizing cart may be used within an internal cabin of a vehicle to decontaminate and disinfect the surfaces of structures, walls, floors, ceilings, and the like within the internal cabin. The structures can include seats, storage containers or bins, tables, and the like. Examples of the subject matter disclosed herein provide safer, more efficient, and more effective sanitation as compared to certain known UV systems, such as manual sanitizing using UV wands and pushing mobile equipment with fixed-in-place UV light sources.

As an example, the wand assembly is a hand held UV wand, which is attached to the UV sanitation cart, such as by a power cord or a power cord and a cooling air hose. The UV wand receives power from the UV sanitation cart. The hand held wand provides an additional sanitizing device. The UV wand can operate in any germicidal UV band, such as between 200 nm to 320. In at least one example, the UV wand includes a UV lamp that is configured to emit UV light having a wavelength within a spectrum of 200 nm to 230 nm band, which is not harmful to human tissue. In at least one embodiment, the UV lamp is configured to emit UV light having a wavelength of 222 UV, which eliminates or otherwise reduces pathogens on a surface of a component and poses no harm to human occupants.

The UV sanitizing system including the wand assembly coupled to the cart can be operated continuously, on a set periodic schedule, or turned on as needed. Power for the system can be provided by batteries and/or a power cord connected to off-board power.

The UV wand attachment (that is, the wand assembly coupled to the cart) allows an individual(s) to disinfect areas that may be shadowed, or likely to be insufficiently disinfected by the primary UV cart UV lighting. The hand held UV wand can be brought very close to and desirably oriented with respect to surfaces. This allows the wand assembly to illuminate and disinfect surfaces unlikely to be disinfected by the other UV light sources of the cart.

Figure 2:
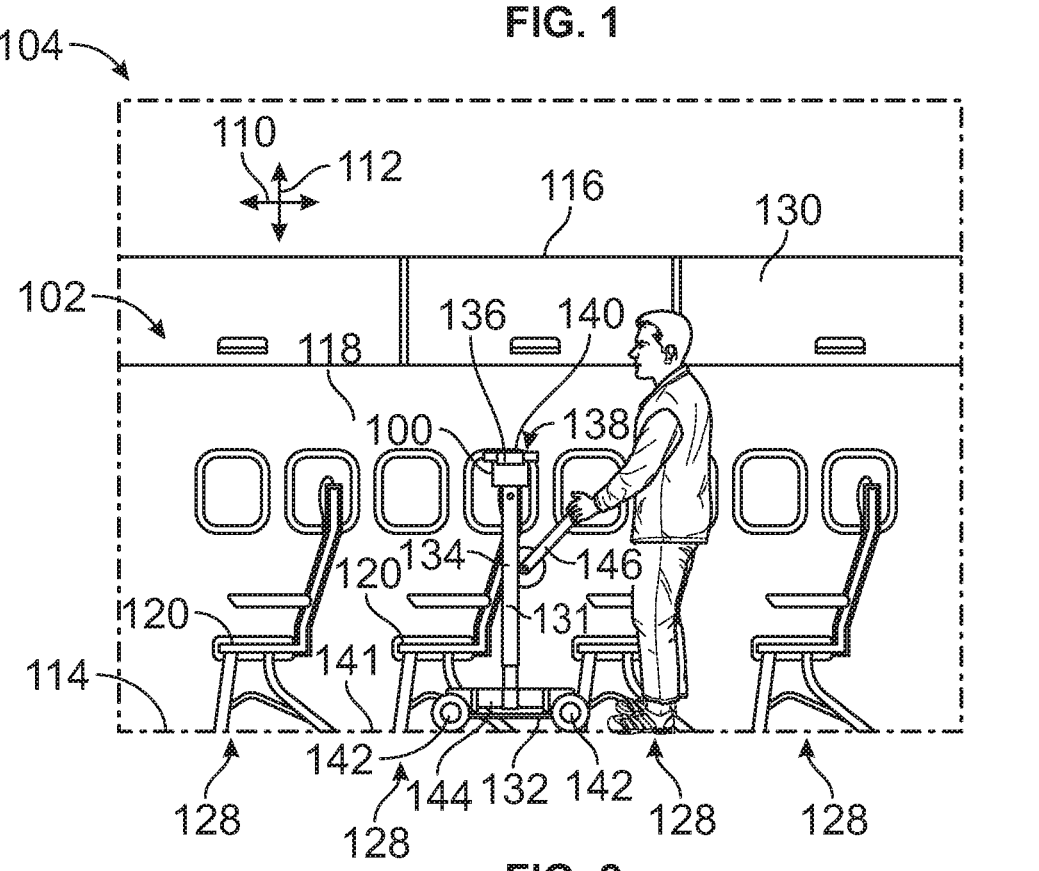
FIG. 2 is a side or outboard view of the internal cabin of the vehicle including the UV light sanitizing cart.

FIG. 1 is a rear or aft-facing view of an internal cabin 102 of a vehicle 104 including a UV light sanitizing system or cart 100 according to an example. FIG. 2 is a side or outboard view of the internal cabin 102 of the vehicle 104 including the UV light sanitizing cart 100. The internal cabin 102 is oriented along a longitudinal or X axis 110, a lateral or Y axis 111, and a vertical (e.g., height) or Z axis 112. The axes 110-112 are mutually perpendicular. The internal cabin 102 is defined by a floor 114, a ceiling 116, and side walls 118 of the vehicle 104. The internal cabin 102 has a plurality of seats 120 for passengers. The seats 120 are arranged in two groups 122, 124 that are spaced apart from each other by an aisle 126. The aisle 126 extends along the longitudinal axis 110. Each of the groups 122, 124 includes seats 120 disposed in multiple rows 128 spaced apart along the length of the cabin 102. Each of the rows 128 is oriented parallel to the lateral axis 111. The cabin 102 also includes storage bins 130 mounted above the seats 120 for storing personal items such as luggage, bags, jackets, and the like. The storage bins 130 can be secured to the ceiling 116 and/or the side walls 118. The UV light sanitizing cart 100 is operable to efficiently, effectively, and consistently sanitize and disinfect surfaces within the internal cabin 102, including for example the seats 120, the storage bins 130, the floor 114, the side walls 118, and/or the ceiling 116.

In a non-limiting example, the vehicle 104 is an aircraft, such as a commercial passenger aircraft, and the internal cabin 102 is a passenger cabin. In another example, the vehicle 104 can be another type of vehicle, such as a rail-based passenger train car, a bus, or the like. The UV light sanitizing cart 100 optionally may be utilized to sanitize other enclosed areas outside of vehicles, such as in buildings. For example, the cart 100 can be used to sanitize office buildings, theatres, restaurants, places of worship, and the like.

The UV light sanitizing system or cart 100 includes a body 131 that has a mobile base 132 and multiple interconnected rigid members 133. The rigid members 133 are supported on the base 132. The rigid members 133 of the body 131 can include, for example, an upright member or trunk 134 coupled to the base 132 and arms 136 that extend from the trunk 134. The rigid members 133 can also include additional components, such as a handle 146, a carrier 214 (described in more detail herein with reference to FIG. 6), and the like. The cart 100 includes a UV light array 138 defined by multiple UV lamps 140. At least some of the UV lamps 140 in the array 138 are mounted to the arms 136. The arms 136 are actuatable to extend from and retract towards the trunk 134. The arms 136 are shown in an extended position in FIGS. 1 and 2, which is the position utilized when operating to disinfect the surfaces of the internal cabin 102. The arms 136 in the extended position are elongated parallel to the lateral axis 111. The extension length of the arms 136 may be controlled based on the space within the cabin 102 and the desired surfaces to disinfect. For example, there are six total seats 120 in each row 128 in the illustrated cabin 102, with three adjacent seats 120 in each group 122, 124. A first arm 136A extends across the three seats 120 in the first group 122, and a second arm 136B extends across the three seats 120 in the second group 122. The UV lamps 140 disposed on the first arm 136A emit UV light on the surfaces of the three seats 120 in the first group 122, and the UV lamps 140 disposed on the second arm 136B illuminate the surfaces of the three seats 120 in the second group 124. As such, in the position of the cart 100 within the cabin 102 shown in FIGS. 1 and 2, the cart 100 concurrently sanitizes all six of the seats 120 in the row 128. The cart 100 moves along a cart path 141, such as forward and rearward along the cart path, to translate the UV light array 138 in directions parallel to the cart path 141. In the illustrated example in which the environment is the internal cabin 102, the cart path 141 is represented by the aisle 126. The cart 100 moves along the length of the aisle 126 to sanitize each of the rows 128 one at a time.

In the illustrated example, the base 132 includes multiple wheels 142 that provide mobility and enable the cart 100 to roll along the length of a path, such as the aisle 126. The base 132 has four wheels 142 in the illustrated example. Alternatively, the base 132 may include continuous tracks with a band of treads that engages the floor 114 instead of the surfaces of the wheels 142. The base 132 may support additional components of the cart 100, such as one or more battery packs 144.

The trunk 134 extends from the base 132 and is oriented along the vertical (or height) axis 112. A handle 146 is coupled to the trunk 134. The handle 146 provides an interface that enables an operator to physically grasp and control the movement of the cart 100, as shown in FIG. 2. The cart 100 is being pushed or pulled by an operator in the illustrated example, such that the cart 100 is operating in a semi-autonomous mode. The semi-autonomous mode, as described herein in more detail, relies on an operator to propel the cart 100 along the aisle 126, but may provide various automated tasks including, for example, terrain following of the UV light array 138 and the arms 136 along the contours of the seats 120 and control feedback to the operator indicating whether the operator should modify the speed or direction of the movement of the cart 100 along the aisle 126 to enhance the sanitizing effectiveness. In the autonomous mode, all operations are automated including the movement of the cart 100 along the aisle 126. For example, an operator may use an input device to selectively wake or turn ON the cart 100 which triggers the cart 100 to perform the sanitization of the internal cabin 102 and then return to a stowed position, as described herein. The handle 146 is optional, as the cart 100 may only operate in the autonomous mode in an example.

As described herein, the UV light sanitizing system or cart 100 also includes a wand assembly that is coupled to (such as moveably secured to) a portion thereof. For example, the wand assembly is coupled to the base 132, and is configured to be moved between a stowed position and deployed position in relation to the base 132.

Figures 3, 4:
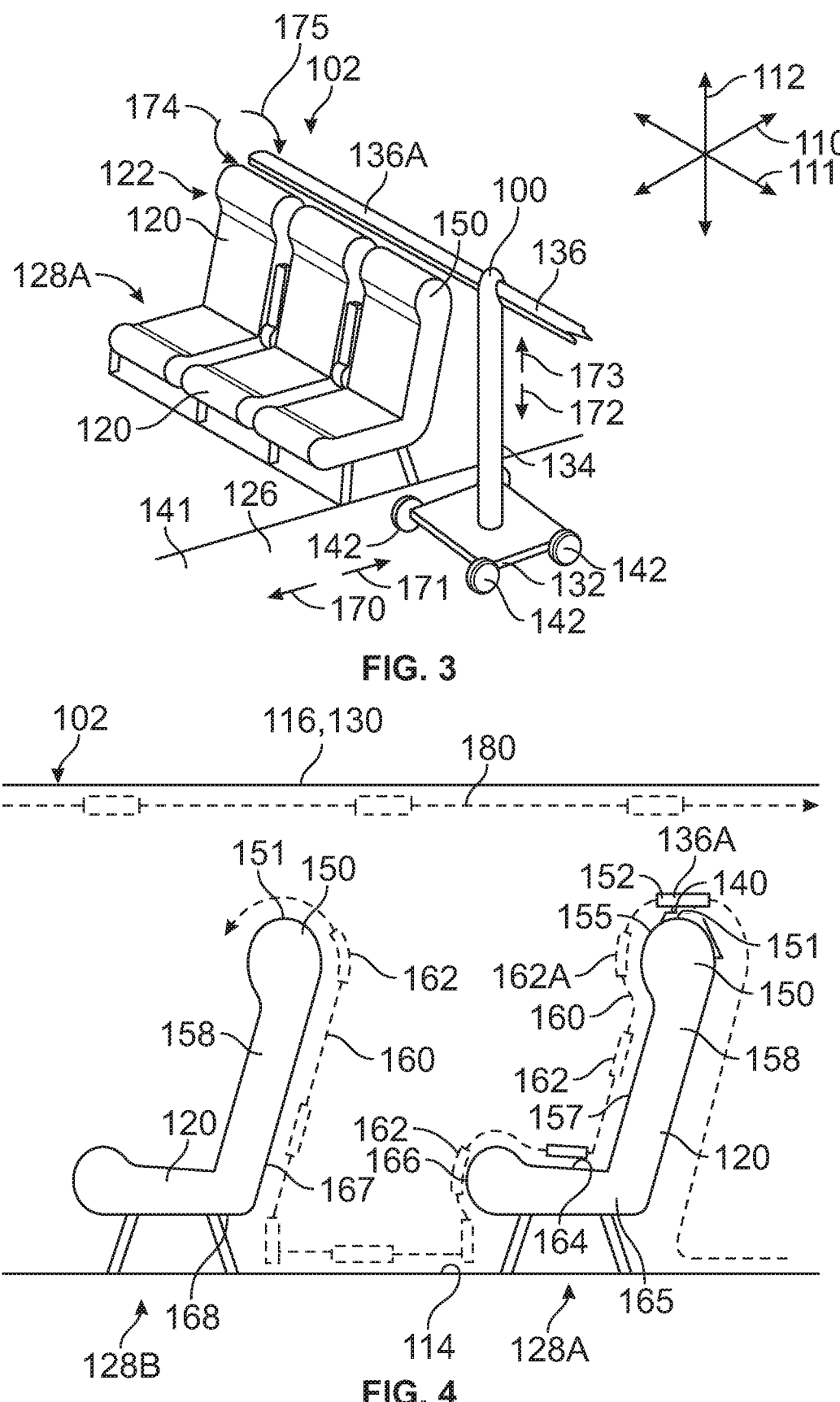
FIG. 3 is a perspective view of the UV light sanitizing cart in the internal cabin, according to an example of the subject disclosure.
FIG. 4 illustrates a side or outboard view of two rows of seats in the internal cabin and shows a movement path of a UV light array of the UV light sanitizing cart over time, according to an example of the subject disclosure.

FIG. 3 is a perspective view of the UV light sanitizing cart 100 in the internal cabin 102 according to an example. The cart 100 in FIG. 3 is disposed in the aisle 126 and the first arm 136A is extended above three seats 120 of the first group 122 of seats 120 in a single (first) row 128A. The handle 146 is omitted in FIG. 3. FIG. 4 illustrates a side or outboard view of two rows 128 of seats 120 and shows the movement path of the UV light array 138 of the UV light sanitizing cart 100 over time according to an example. The two rows include the first row 128A of seats 120 shown in FIG. 3 as well as the row 128B of seats 120 in front of the first row 128A. FIGS. 3 and 4 show the terrain following capability of the UV light sanitizing cart 100 which achieves effective, efficient, and consistent disinfection of the various surfaces in the cabin 102. At the position shown in FIG. 3, the arm 136A is disposed above the headrests 150 of the seats 120 and the UV lamps 140 (shown in FIG. 1) disposed on the arm 136A emit UV light onto the tops of the headrests 150.

Referring to FIG. 3, the UV light sanitizing cart 100 can translate and rotate the UV lamps 140 in the UV light array 138 (shown in FIG. 1) relative to the seats 120 and other structures in the internal cabin 102 to emit the UV light within a designated proximity of the surfaces of the structures. The designated proximity may be a few inches, such as 2 inches, 4 inches, or the like. In the illustrated example, the cart 100 moves the UV lamps 140 along the longitudinal or X axis 110 by moving the cart 100 along the aisle 126. For example, in the autonomous mode, the wheels 142 are propelled to drive the cart 100. In the semi-autonomous mode, the cart 100 may instruct the operator how to push or pull the cart 100, such as by providing feedback on the speed of movement and direction along the longitudinal axis 110. The arms 136 are translatable along the vertical or Z axis 112 to control the height of the UV lamps relative to the surfaces of the seats 120 and other structures. For example, the trunk 134 may be telescopic to mechanically raise and lower the arms 136. The arms 136 may be rotatable about the lateral or Y axis 111 to aim the UV light towards the surfaces of the seats 120 and other structures.

Referring now to FIG. 4, the current position of the first arm 136A in the position shown in FIG. 3 is indicated by the solid-line rectangle 152 that is disposed above the top 151 of the headrest 150 of the seat 120 in the first row 128A. The UV light emitted by the illustrated UV lamp 140 on the arm 136A illuminates the top 151 of the headrest 150. FIG. 4 shows a cleaning path 160 of the first arm 136A over time according to an example. The dashed rectangles 162 represent the positions of the first arm 136A at subsequent times as the cart 100 moves the arm 136A along the cleaning path 160. For example, after sanitizing the top 151 of the headrest 150, the first arm 136A moves along the cleaning path 160 to the position 162A at which the UV light is emitted from the UV lamp 140 onto a front 155 of the headrest 150. Although only one seat 120 is shown per row in FIG. 4, it is recognized that all three of the seats 120 in the block shown in FIG. 3 may be concurrently receiving the UV light at the same respective surfaces of the seats 120. Furthermore, although several dashed rectangles 162 are shown at different positions, in an example, the UV light is continuously emitted from the arm 136A along the entire length of the cleaning path 160. The illustrated dashed rectangles 162 do not represent the only positions at which UV light is emitted.

The cleaning path 160 of the first arm 136A (and UV lamps 140 thereon) extends along a front 157 of the seat back 158 (of each of the seats 120 in the block) to a top 164 of the seat bottom 165, then along a front 166 of the seat bottom 165. The UV light is subsequently emitted underneath the seats 120 and then emitted towards the floor 114 between the two rows 128A, 128B. Then, the arm 136A moves to have the UV lamps 140 emit UV light underneath the seats 120 in the next row 128B before emitting the UV light onto a back 167 of the seat back 158 (of each of the seats 120 in the block) from a bottom 168 of each seat 120 towards the top 151 of the headrest 150.

The movement of the arm 136A along the cleaning path 160 is autonomous or at least semi-autonomous. In an example, the only movement that receives manual input in the semi-autonomous mode is movement along the longitudinal axis 110. The cart 100 is able to provide compound movements, which refer to concurrent movements along multiple axes and/or articulation points. For example, to accomplish the transition from the position indicated 152 in FIG. 4 to the position 162A, the arm 136A holding the UV lamps 140 is moved in a forward direction 170 (shown in FIG. 3) along the longitudinal axis 110, is lowered in a downward direction 172 (FIG. 3) along the vertical axis 112, and is rotated in a counterclockwise direction 174 (FIG. 3) about the lateral axis 111. These movements may be performed concurrently to enable the arm 136A to sweep along the contour of the headrest 150. In the illustrated example, the movement in the forward direction 170 can be accomplished by driving the entire cart 100 forward, but alternatively can be provided by actuating the trunk 134 and/or the arm 136A relative to the base 132 such that the cart 100 remains in a fixed position on the aisle 126. To achieve other positions of the arm 136A along the cleaning path 160, the arm 136A can be moved in a rearward or aft direction 171 along the longitudinal axis 110, in an upward direction 173 along the vertical axis 111, and in a clockwise direction 175 about the lateral axis 111. Although not shown in FIG. 3, the cart 100 may be able to move the arms 136 along other planes and axes of rotation as well, as described herein.

The cleaning path 160 traces the contours of the seats 120 and other structures present in the cabin 102. In an example, the cleaning path 160 is designed to allow the UV lamps 140 to be within the designated or predetermine proximity or range of the surfaces for providing effective and efficient dosages of UV light. For example, by controlling the UV lamps 140 to be within a few inches of the surfaces, a designated dosage can be applied without requiring substantial amounts of power of the UV light or time of exposure. Limiting the power requirement is energy efficient, and limiting the time of exposure is efficient with respect to time. For example, by emitting the UV light closer to the target surfaces, the cart 100 can provide consistent and effective disinfection of the cabin 102 at less time and power consumption than known systems. Furthermore, the UV dosage applied to the surfaces by the cart 100 may be greater and therefore more effective at neutralizing microbes than known systems that use approximately the same amount of power and/or time to clean because the range from the UV lamp to the target surface is less.

Optionally, the cleaning path 160 shown in FIG. 4 may be a first path that is followed by the UV light sanitizing cart 100 along the length of the aisle 126 in one direction, such as in the forward direction 170. The UV light sanitizing cart 100 may then follow a second cleaning path 180 as the cart 100 moves in the opposite, rearward direction 171 along the aisle 126. The second cleaning path 180 follows the contours of the ceiling 116 and/or storage bins 130 above the seats 120. The UV light is emitted upwards onto the ceiling 116 and/or storage bins 130 instead of downward onto the seats 120 and floor 114. In a non-limiting example, by simply moving the cart 100 down the length of the aisle 126 and then back to the starting position, the cart 100 can sanitize the surfaces of the structures, walls, floors, and the like.

Figure 5:
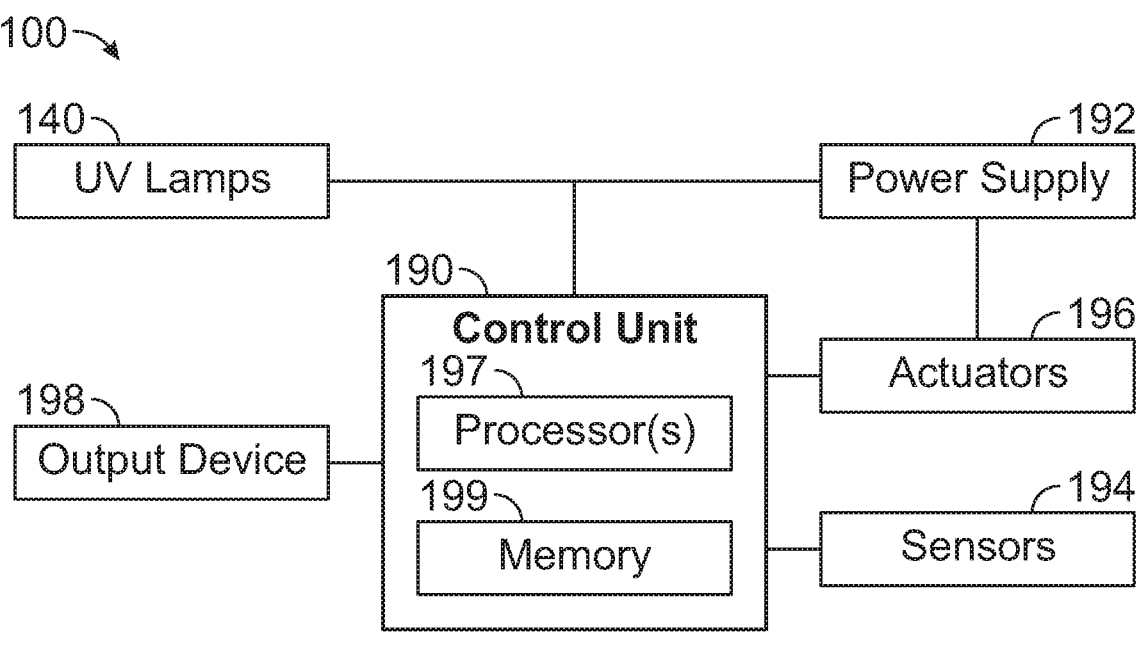
FIG. 5 is a is a schematic diagram of the UV light sanitizing cart, according to an example of the subject disclosure.

FIG. 5 is a schematic diagram of the UV light sanitizing cart 100 according to an example. The sanitizing cart 100 includes the UV lamps 140 that represent the array 138 (shown in FIG. 1), a control unit 190, a power supply 192, sensors 194, actuators 196, and an output device 198. The actuators 196 refer to mechanical actuators, motors, and drive systems that produce the automated movements of the cart 100, such as the rotation of the wheels 142, the extension and retraction of the trunk (or support member) 134 and the arms 136, the rotation of the arms 136 relative to the trunk 134, and the like.

The power supply 192 provides electrical power to the UV lamps 140 to power the generation of the UV light. The power supply 192 also provides power to both the actuators 196, the control unit 190, the sensors 194, and the output device 198. Various electrically conductive wires and/or cables may conduct the power from the power supply 192 to the UV lamps 140, actuators 196, the control unit 190, the sensors 194, and the output device 198. The power supply 192 may include or represent any onboard energy storage devices or power generation components, including but not limited to the batteries 144 shown in FIGS. 1 and 2. The power supply 192 can also include capacitors, photovoltaic cells, and/or the like. Optionally, the power supply 192 may be power cable that plugs into a source disposed offboard the cart 100, such as an electrical system of the vehicle 104 (or building) that includes the internal cabin 102. The power cable may be able to extend the entire length of the internal cabin 102 to enable the cart 100 to sanitize the entire cabin 102 without removing the cable from the outlet to plug into another outlet. In another example, the power supply 192 may be a generator or electrical storage device that is off-board the cart 100 but discrete from the vehicle 104. For example, the power supply 192 may be disposed in a backpack carried by an operator or may be disposed on a side cart that is tethered to the UV light sanitizing cart 100.

In at least one embodiment, at least one of the UV lamps 140 is on or within a wand assembly. For example, the wand assembly including at least one UV lamp 140 is coupled to a portion of the UV light sanitizing cart 100, such as the body 131 shown in FIGS. 1 and 2.

The control unit 190 is operatively connected to the UV lamps 140, the actuators 196, the sensors 194, and the output device 198 via wired and/or wireless communication pathways. The control unit 190 generates control signals that control the operations of the UV lamps 140, such as On/Off states, the amplitude or power output of the UV light that is generated, and optionally also the wavelengths of the UV light. The control unit 190 also generates control signals for controlling the actuators 196 and the output device 198. These control signals may be generated based on sensor signals received from the sensors 194. The control unit 190 represents hardware circuitry that includes and/or is connected with one or more processors 197 (e.g., one or more microprocessors, integrated circuits, microcontrollers, field programmable gate arrays, etc.). The control unit 190 includes and/or is connected with a tangible and non-transitory computer-readable storage medium (e.g., memory) 199. For example, the memory 199 may store programmed instructions (e.g., software) that is executed by the one or more processors 197 to perform the operations of the control unit 190 described herein.

The sensors 194 can include proximity sensors, vision sensors, and the like. The sensors 194 can utilize ultrasound, cameras (e.g., in the visual and/or infrared wavelength ranges), optical range sensing (e.g., light detection and ranging (LIDAR)), and/or the like. The sensors 194 are used for object avoidance to prevent collisions between the cart 100 and objects and structures in the cabin 102. In certain examples, the sensors 194 are also utilized for spatial recognition to guide the arms 136 with the UV lamps 140 along the cleaning paths 160, 180 shown in FIG. 4. For example, the sensors 194 can be utilized by the control unit 190 to determine the current position of the cart 100 and/or components thereof relative to the internal cabin 102.

In one non-limiting example, the memory 199 stores a map of the environment within the internal cabin 102. The map may be three-dimensional, and may have a coordinate system. For example, all of the rows 128 of seats 120 have known coordinates within the map. Furthermore, the cleaning paths 160, 180 can be pre-programmed routes within the coordinate system of the map. The control unit 190 in the autonomous mode can move to or remain in a designated reference location within the cabin 102. The movement of the cart 100 can be tracked by the control unit 190 based on mechanical elements, such as gears, linkages, actuators 196, and the like. By starting at the reference location and then tracking the subsequent movement from the reference location, the control unit 190 can correlate or register the movements in the physical space with corresponding movement in the virtual space of the 3D map. For example, the control unit 190 can determine that present location of the cart 100 in the cabin 102 based on consulting the 3D map and tracking the movement of the cart 100 from the reference location. The movement of the cart 100 may be tracked, in part, by monitoring the positioning of the wheels 142 which indicate direction of movement and monitoring the rotations of the wheels 142 (or associated components). Similar tracking of the arms 136 via the various actuators 196 and other mechanical elements that control the movement of the arms 136 can be utilized by the control unit 190 with the 3D map to enable the control unit 190 to control the terrain following shown and described in FIG. 4. In this example in which the movement of the UV array 138 is controlled based on a stored map of the cabin 102, the sensors 194 are used for object avoidance. For example, the sensor signals can indicate when modifications to the map should be performed to avoid objects that are not accounted for in the map, such as a bag left on a seat, or the like.

In another example, the sensors 194 can be used to guide the movement of the cart 100 instead of using the map. For example, the control unit 190 may be a vision-based system. The sensors 194 may provide the control unit 190 with image data, range data, and the like. The processor(s) 197 can analyze the sensor data and perform object detection, such as to identify a seat 120 in the image data. Based on the identified seat and the distance to the seat based on the sensor data, the control unit 190 generates control signals to control the arms 136 to approach the surfaces of the seat 120 and move along the surfaces as shown in the cleaning paths 160, 180 shown in FIG. 4.

The output device 198 can include or represent lights, speakers, a display screen, vibration packs, and/or the like for providing alerts and notifications to nearby persons. For example, the output device 198 can have flashing lights and/or emit beeping sounds when the cart 100 is operating in the autonomous mode to alert persons in the vicinity of the cart 100 that the cart 100 is moving. When in the semi-autonomous mode with a human operator present, the output device 198 can be used to instruct or modify the movement of the operator for the purpose of improving the effectiveness, efficiency, and/or consistency of the disinfection process. For example, there may be a designated speed or range of speeds that the cart 100 is moved along the aisle 126 to yield favorable or satisfactory disinfection performance, which is based in part on the time of exposure of the UV light on the target surfaces. The operator can be informed of the actual speed of the cart 100 relative to the designated speed using one or more of the following: a pacing light on the cart 100 that illuminates in different colors and blinking rates depending on whether or not the speed is correct, too fast, or too slow; the handle 146 vibrates at different frequencies and/or intensities depending on whether or not the speed is correct, too fast, or too slow; and/or an audio tone that changes sound and pulse rates depending up whether or not the speed is correct, too fast, or too slow.

Figure 6:
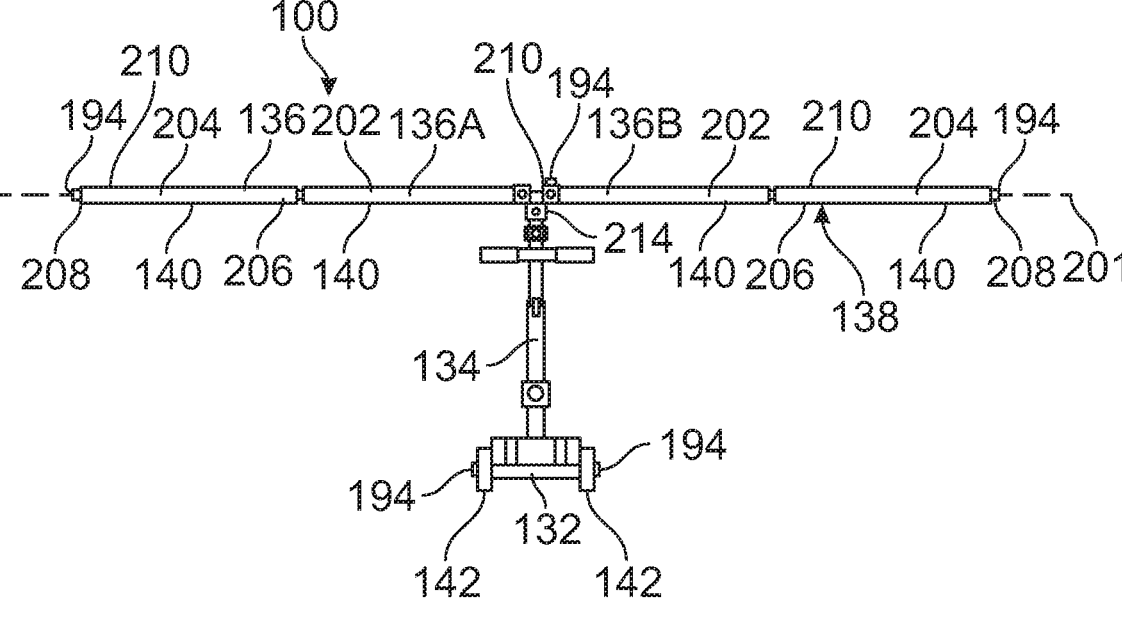
FIG. 6 is a rear view of the UV light sanitizing cart with arms raised and extended, according to an example of the subject disclosure.

FIG. 6 is a rear view of the UV light sanitizing cart 100 with the arms 136 raised and extended according to an example. With the arms 136 extended, the UV light array 138 is linearly elongated along an array axis 201. The UV light array 138 emits UV light along the length of the array 138 to essentially provide a wall or sheet of UV light. In one or more examples, the cart 100 is autonomously controlled to rotate the UV light array 138 about the array axis 201 when desired to enable the UV light array 138 to follow the contours of the component surfaces within the sanitizing environment and aim the UV light towards the component surfaces as the surface curve and intersect. The cart 100 is also autonomously controlled to translate the UV light array 138 along two axes that are perpendicular to each other and to the array axis 201. For example, when the array axis 201 is parallel to the lateral axis 111 shown in FIGS. 1 and 3, the cart 100 can translate the UV light array 138 vertically along the vertical or height axis 112 and longitudinally along the longitudinal axis 110 during the sanitization process.

The first and second arms 136A, 136B may be mirror replicas of each other, so only one arm 136 is described to represent both. The arm 136 includes multiple interconnected members including at least an inner member 202 and an outer member 204. The inner member 202 is connected to the trunk 134 and connects the outer member 204 to the trunk 134. The UV light array 138 includes at least one elongated UV lamp 140 mounted to each of the inner member 202 and the outer member 204. The UV lamps 140 are elongated along at least a majority of the length of the arm 136 to emit essentially a wall of UV light. The UV lamps 140 are only disposed along one side 206 of the members 202, 204 in the illustrated example, but in other examples additional UV lamps 140 may be disposed at the end 208 of the outer member 204 and/or along the opposite side 210 of the members 202, 204 as well. In the raised and extended position as shown, the arms 136A, 136B extend parallel to each other and parallel to the floor (e.g., perpendicular to the axis of the trunk 134).

The illustrated example also shows various locations of sensors 194 onboard the cart 100. For example, the cart 100 can include sensors 194 on the wheels 142 or the base 132 that are used to determine the proximity of the base 132 to nearby objects for object avoidance. Additional sensors 194 can be mounted at the ends 208 of the arms 136A, 136B to determine the proximity to nearby objects and/or structures. For example, the sensors 194 on the ends 208 can be used to determine a distance that the arms 136A, 136B extend from the trunk 134. Another sensor 194 can be mounted at a top 212 of the trunk 134 which can be used to determine the proximity of the arms 136A, 136 to surfaces above the cart 100.

In an example, the cart 100 includes a carrier or head 214. The carrier 214 is mounted to the trunk 134 and can rotated relative to the trunk 134 about the vertical axis 112 shown in FIG. 3. The carrier 214 may also be rotatable relative to the trunk 134 about the lateral axis 111. The arms 136A, 136B may be mechanically coupled to the carrier 214, such that rotation of the carrier 214 causes similar movement of the arms 136A, 136B (and the UV light array 138) relative to the trunk 134. The arms 136A, 136B can pivot on hinges at the interface with the carrier 214.

FIG. 7 is a view of the UV light sanitizing cart 100 stowed within a monument 220 within the internal cabin 102 according to an example. The cart 100 is shown with the arms 136 in a collapsed state relative to the trunk 134. In the collapsed state, the arms 136 are retracted to extend parallel to the trunk 134 and are disposed adjacent the trunk 134. The arms 136 may physically abut (e.g., contact) the trunk 134 in the collapsed state. The arms 136 retract by pivoting at the hinges of the carrier 214. The monument 220 in which the cart 100 is stowed may be a closet, vestibule, or another compartment. In the autonomous mode, the control unit 190 may retract the arms 136 and drive the cart 100 into a cavity 222 within the monument 220 upon completion of a sanitizing task. Optionally, a beacon device may be disposed within the monument 220 that communicates with the cart 100 to enable the cart 100 to return to the home, stowed position.

In an example, the control unit 190 self-monitors the activities of the UV light sanitizing cart 100 by logging cleaning events in the memory 199. For example, during the sanitizing process or upon returning to the home, stowed position, the processor(s) 197 may record a new record in a log or database. The record may provide the day and time of the most recent cleaning event, and optionally may include additional details, such as the elapsed time for the entire cleaning event, a calculated dosage of UV light applied to the surfaces, an identity of the internal cabin 102 and/or the vehicle 104 that is sanitized, any errors or unanticipated objects detected during the cleaning event, whether the cart 100 was in full autonomous mode or semi-autonomous mode, and the like. The log of cleaning events can be used as evidence that the cabin 102 was properly sanitized by a machine, without the risk of human error or negligence. The log can be copied and/or transmitted remotely from the memory 199 as desired for data collection, sharing, and the like.

FIGS. 8 and 9 show two different actuator mechanisms for raising and lowering the arms 136, and therefore the UV light array 138, relative to the trunk 134. The angle between each arm 136 and the trunk 134 is referred to as theta (θ). FIG. 8 shows a curved rack and pinion actuator 230 that includes a curved gear 232 and a circular drive gear 234. FIG. 9 shows a linear actuator 240 that includes a piston 242 within a cylinder 244. Each actuator 230, 240 receives power from the power supply 192 and control signals from the control unit 190 to control the angle theta between the respective arm 136 and the trunk 134.

Figure 10:
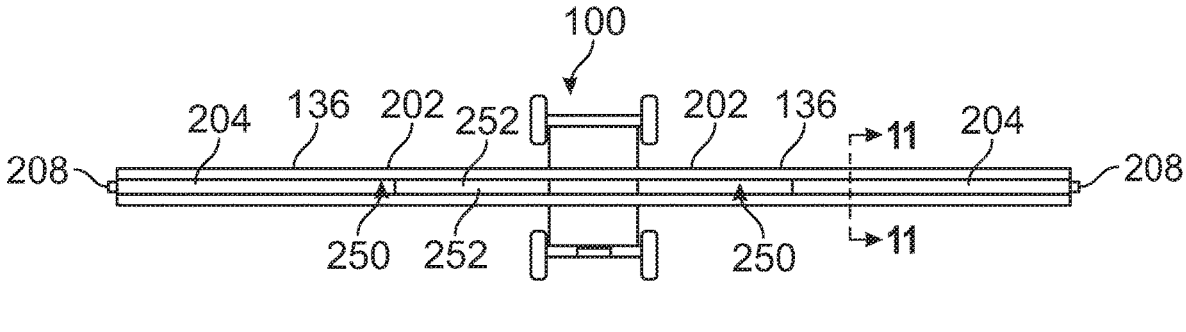
FIG. 10 is a top-down view of the UV light sanitizing cart, according to an example of the subject disclosure.
Figure 11:
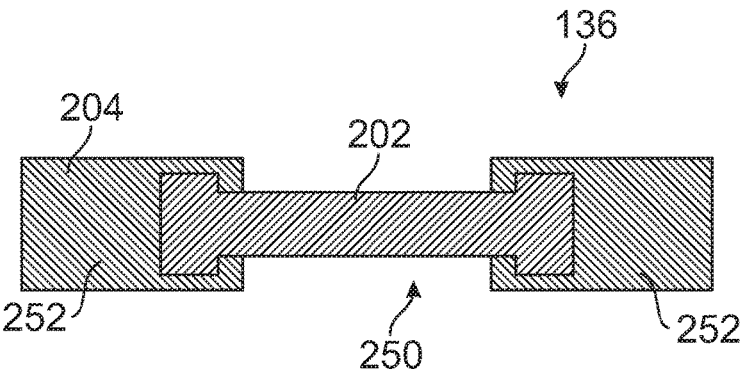
FIG. 11 is a cross-section view of an inner member and an outer member of one of the arms of the UV light sanitizing cart, according to an example of the subject disclosure.

FIG. 10 is a top-down view of the UV light sanitizing cart 100 according to an example. FIG. 11 is a cross-section view of the inner member 202 and the outer member 204 of one of the arms 136 of the UV light sanitizing cart 100 according to an example. The cross-section is taken along line 11-11 in FIG. 10. In the illustrated example, the outer member 204 of each arm 136 nests into the inner member 202. For example, the inner member 202 defines a track 250 between two rails 252, and the outer member 204 slides within the track 250 to control the length or extension of the arm 136. Although each arm 136 has two members 202, 204 in the illustrated example, in other examples the arms 136 may have only one member or at least three members. For example, another member may be coupled to the outer member 204 and controllable to extend beyond the end 208 of the outer member 204 to increase the extension length. Although not shown, the UV lamps 140 of the array 138 are mounted to each of the members 202, 204 as described above.

Figure 12A:
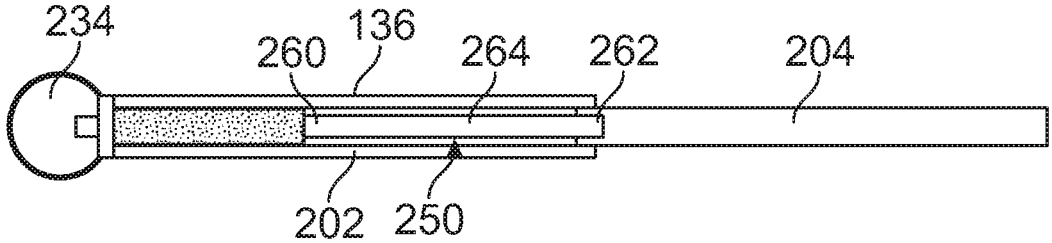
FIG. 12A shows the outer member of an arm extended relative to the inner member.
Figure 12B:
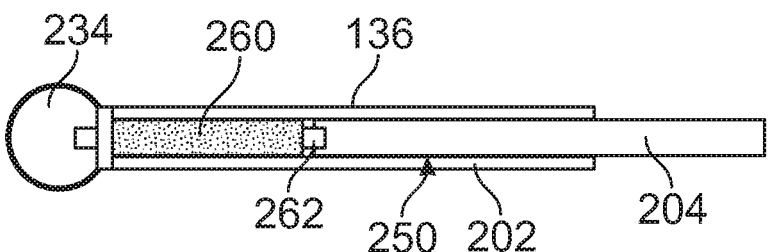
FIG. 12B shows the outer member retracted relative to the inner member.
Figure 13:
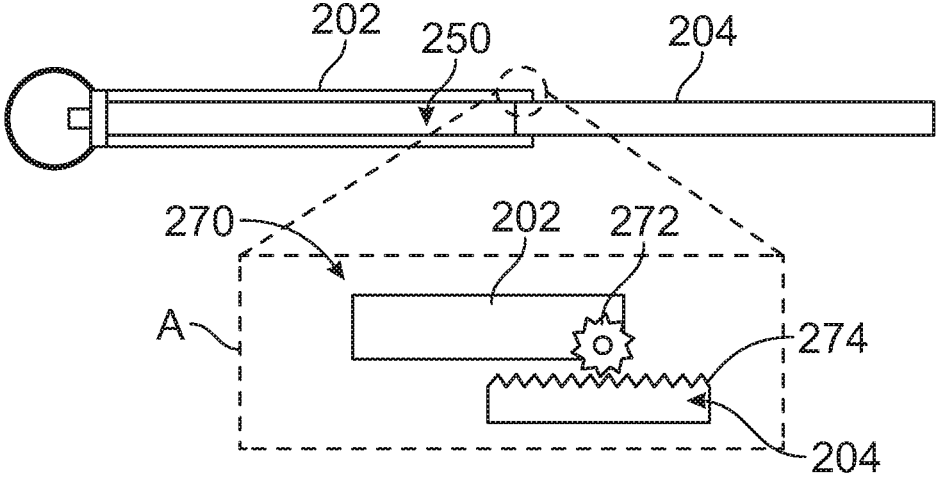
FIG. 13 shows a rack and pinion or gear driven actuator for controlling the extension of the outer member relative to the inner member.

FIGS. 12A, 12B, and 13 illustrate two different actuator mechanisms for adjusting the extension length of the arms 136 (e.g., adjusting the lateral width of the UV light array 138). FIGS. 12A and 12B show a linear actuator 260 that is mounted to the inner member 202 and mechanically coupled to the outer member 204. For example, the end 262 of the translating piston 264 of the actuator 260 is coupled to the outer member 204 such that extension of the piston 264 pushes the outer member 204 along the track 250 in a direction away from the trunk 234 and retraction of the piston 264 pulls the outer member 204 towards the trunk 234. FIG. 12A shows the outer member 204 extended relative to the inner member 202, and FIG. 12B shows the outer member 204 retracted. FIG. 13 shows a rack and pinion or gear driven actuator 270. The enlarged inset portion A in FIG. 13 shows that a gear drive 272 may be mounted to the inner member 202 and the outer member 204 may include a row 274 of gear teeth that engages the gear drive 272. Powered rotation of the gear drive 272 causes translation of the outer member 204 relative to the inner member 202 along the track 250.

Figure 14D:
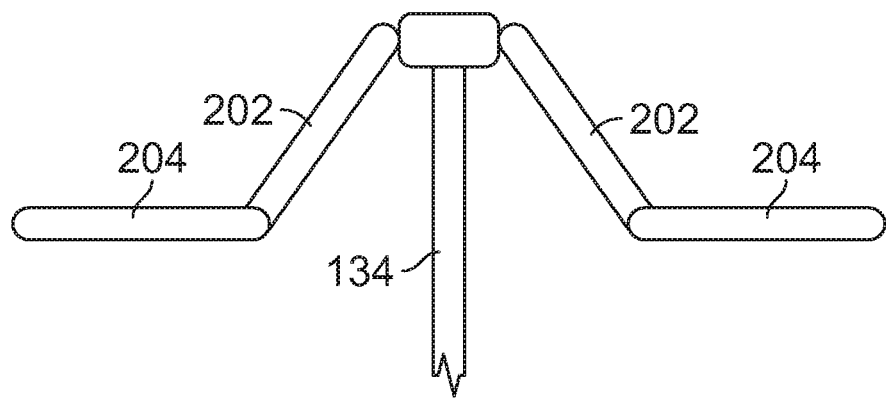
Figure 14E:
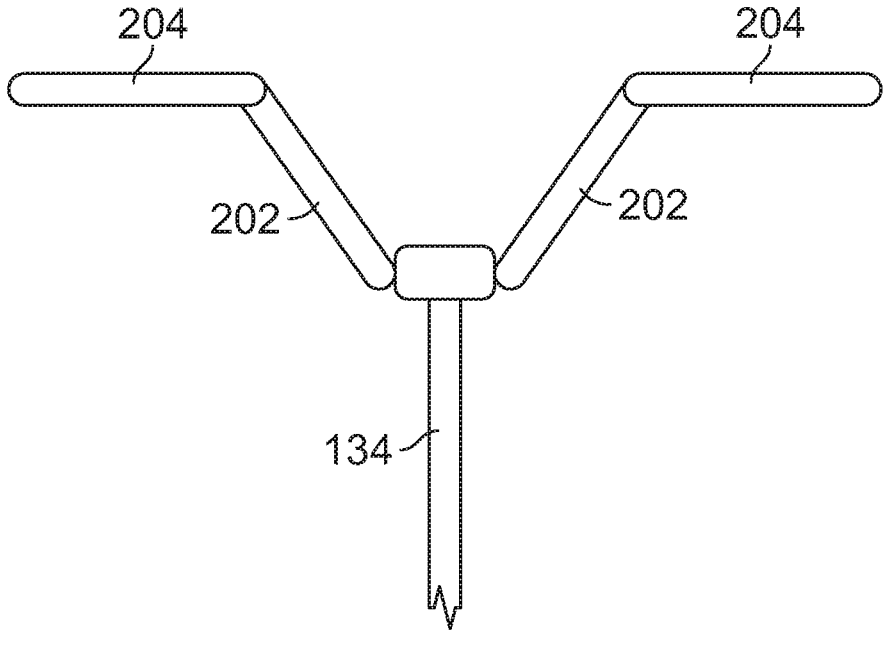

FIGS. 14A-E depict the arms 136 and the trunk 134 of the UV light sanitizing cart 100 according to another example in which the outer members 204 can pivot relative to the inner members 202. In FIG. 14A, the outer members 204 are pivoted downward relative to the inner members 202 to define a right angle between the inner and outer members 202, 204. In FIG. 14B, the outer members 204 extend upward to define right angles with the inner members 202. In FIG. 14C, both arms 136A, 136B extend upward from the trunk 134 and are approximately parallel to each other and to the trunk 134. The inner and outer members 202, 204 are coaxial in FIG. 14C. In FIGS. 14D and 14E, the outer members 204 extend horizontally at approximately right angles relative to the trunk 134, but the inner members 202 extend at oblique angles relative to the trunk 134. The ability to independently control the extension angles of the inner and outer members 202, 204 relative to the trunk 134 and relative to each other can enable the control unit 190 to aim the UV light at various different surfaces at the same time, such as to illuminate both the seats 120 and the side walls 118 of the inner cabin 102.

FIG. 15 depicts an outer array carrier 280 that is mounted to the inner member 202 of an arm 136 of the UV light sanitizing cart 100 according to an example. The outer array carrier 280 is translatable relative to the inner member 202 along the track 250. The outer array carrier 280 is coupled to the outer member 204 and is configured to rotate the outer member 204 relative to the inner member 202. The ability to independently rotate the inner member 202 and the outer member 204 can enable the UV lamps 140 to provide an organic sweeping motion along the target surfaces that are being sanitized. The rotation may also alleviate inconsistent sanitization attributable to shadows by reducing the presence of shadows.

FIG. 16 depicts a steering mechanism 290 for controlling the position of the wheels 142 of the UV light sanitizing cart 100 according to an example. The actuator 290 includes a servo steering motor 292 that is coupled to a tie rod or linkage 294. The servo motor 292 is controlled by the control unit 190 to rotate a set amount either clockwise or counterclockwise, which moves the tie rod 294. The tie rod 294 is connected at each end to a corresponding wheel carrier assembly 296.

Figure 17:
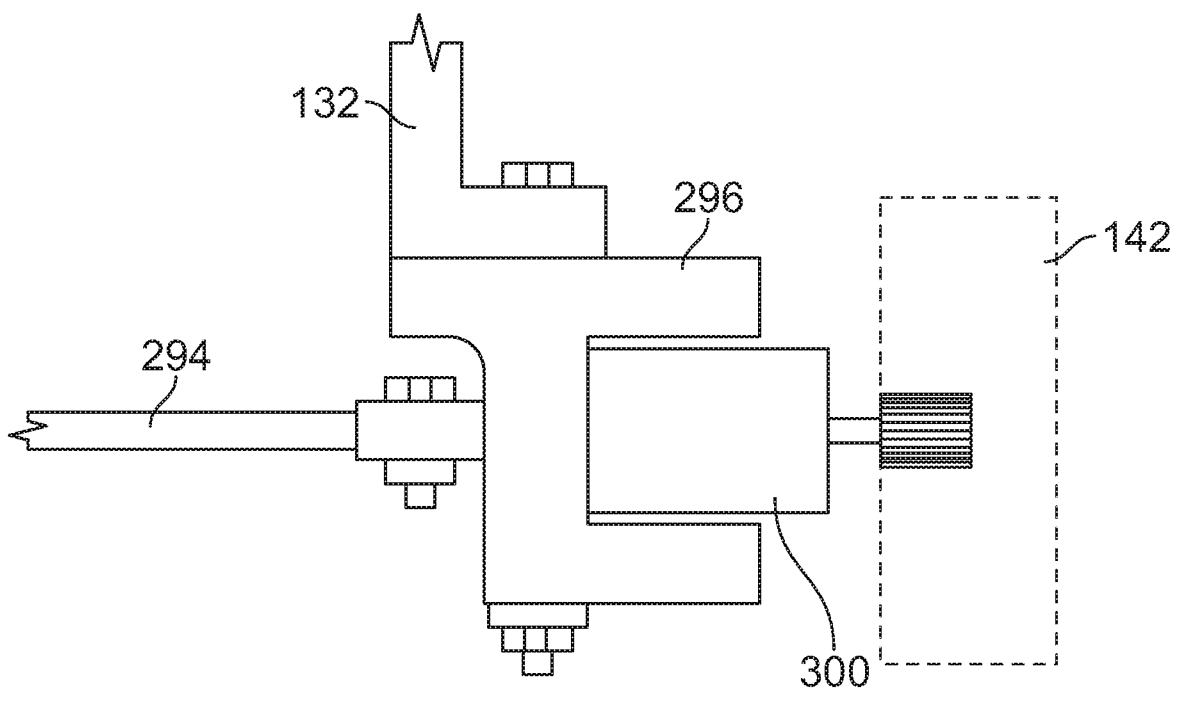
FIG. 17 shows a wheel carrier assembly of the steering mechanism shown in FIG. 16.

Reference is now made to FIG. 17, which shows one of the wheel carrier assemblies 296 in more detail. The carrier assembly 296 includes a traction motor 300 that generates torque for the wheel 142. The carrier assembly 296 is pivotably or rotatably secured to the frame or base 132 of the cart 100. The movement of the tie rod 294 by the servo steering motor 292 causes the carrier assembly 296 to turn or pivot relative to the base 132. Because the carrier assembly 296 includes the wheel 142, as the carrier assembly 296 pivots the cart 100 turns.

Figure 18:
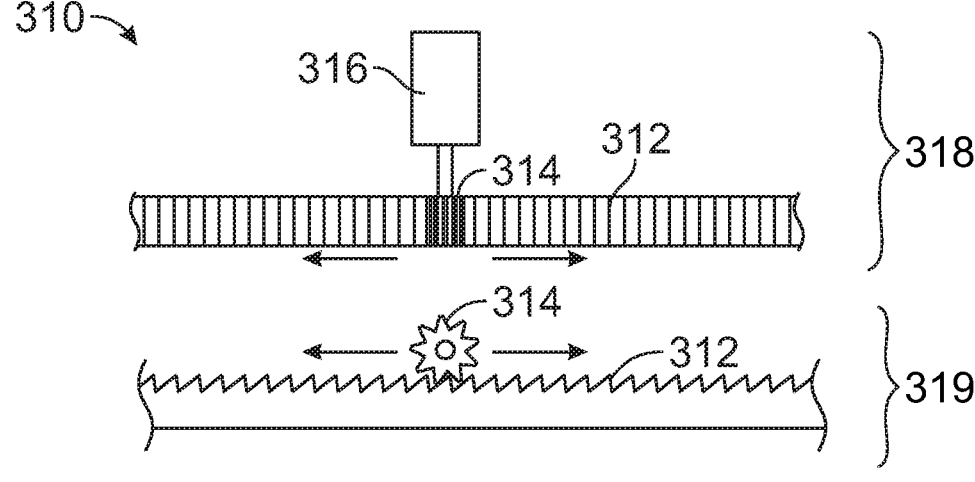
FIG. 18 shows a rack and pinion mechanism for steering the UV light sanitizing cart as an alternative to the steering mechanism shown in FIGS. 16 and 17.

FIG. 18 shows a rack and pinion mechanism 310 for steering the cart 100 as an alternative to the steering mechanism 290 shown in FIGS. 16 and 17. For example, the tie bar or linkage 294 may include a row 312 of gear teeth that engage a drive gear 314 coupled to a motor 316. The rotation of the drive gear 314 by the motor 316 causes the movement of the tie bar 294 that changes the angle of the wheels 142 as described above. FIG. 18 shows both a top-down view 318 and a side view 319 of the mechanism 310.

Figure 19:
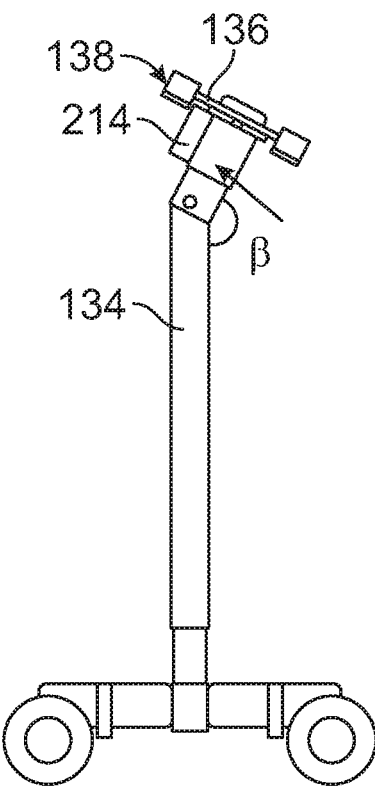
FIG. 19 shows a carrier of the UV light sanitizing cart angled relative to the trunk, according to an example of the subject disclosure.

FIG. 19 shows the carrier 214 of the UV light sanitizing cart 100 angled relative to the trunk 134. The carrier 214 can rotate relative to the trunk 134 about the lateral axis 111 shown in FIG. 3 to provide a range of beta (β) angles. The control unit 190 controls an actuator to set the beta angle. The arms 136 and the UV light array 138 rotate with the carrier 214. As such, the control unit 190 may rotate the carrier 214 to change the orientation of the UV light array 138 relative to the internal cabin 102 for aiming the UV light towards the surfaces. For example, the different orientations of the arm 136 along the cleaning path 160, as schematically depicted in FIG. 4, may be accomplished by rotating the carrier 214 to change the beta angle.

Figure 20:
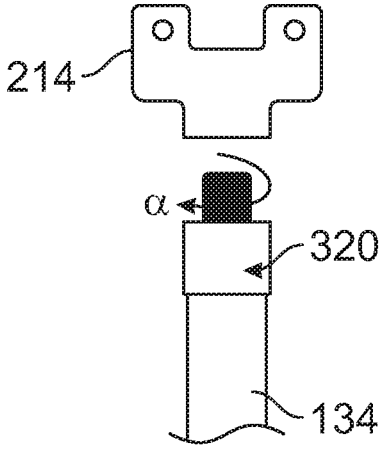
FIG. 20 depicts an actuator that can be used to rotate the carrier about a vertical axis, according to an example of the subject disclosure.

FIG. 20 depicts an actuator 320 that can be used to rotate the carrier 214 about the vertical axis 112 shown in FIG. 3. Rotating the carrier 214 relative to the trunk 134 about angle alpha (α) can spin the arms 136 and the UV light array 138 relative to the trunk 134 and the base 132.

Figure 21A:
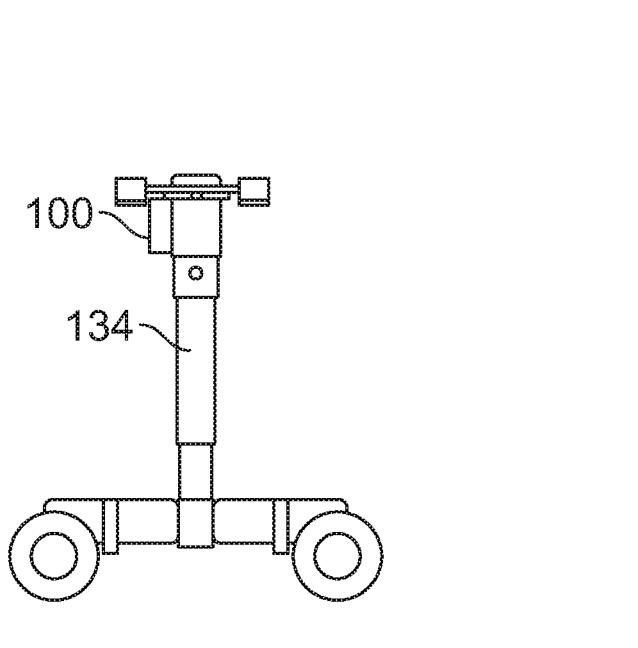
FIG. 21A shows the UV light sanitizing cart at a first height.
Figure 21B:
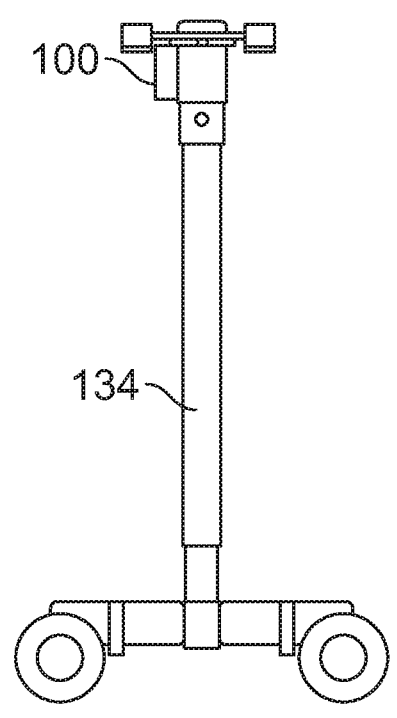
FIG. 21B shows the UV light sanitizing cart at a second height that is taller than the first height due to extension of the trunk.
Figure 21C:
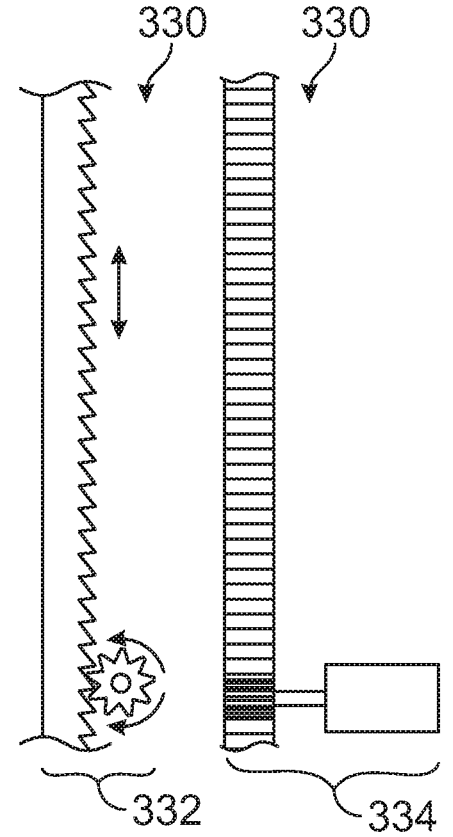
FIG. 21C depicts both a side view and a top-down view of a rack and pinion actuator for extending and retracting the trunk, according to an example of the subject disclosure.

FIGS. 21A-C show that a rack and pinion actuator 330 can be used to extend and retract the telescopic trunk 134 of the UV light sanitizing cart 100. FIG. 21A shows the cart 100 at a first height. FIG. 21B shows the cart 100 at a second height that is taller than the first height due to extension of the trunk 134. FIG. 21C depicts the rack and pinion actuator 330 in both a side view 332 and a top-down view 334.

FIG. 22 depicts the base 132 of the UV light sanitizing cart 100 according to an alternative example. In the example described above in FIGS. 1-3, the trunk 134 is fixed in place on the base 132 and the entire cart 100 is moved or driven forward or backward along the aisle 126 to move the arms 136 and the UV light array 138 along the longitudinal axis 110. In FIG. 22, the trunk 134 is translatable relative to the base 132 along at least one axis. Optionally, the trunk 134 is able to translate both longitudinally and laterally relative to the base 132 while remaining mounted on the base 132. For example, the trunk 134 may be coupled to the base 132 via a belt and pulley mechanism 340 or a tracked rack and pinion mechanism 342 that enables the trunk 134 to move along one axis. Either mechanism 340, 342 may be able to slide along the perpendicular axis via carrier wheels 343 within a track 344 defined by the base 132. Having a translatable trunk 134 enables the base 132 of the cart 100 to pull into position between two rows 128, for example, and then remain stationary in that position while the trunk 134, the carrier 214, and/or the arms 136 translate and/or rotate to provide the terrain following of the UV light array 138. Once a segment of the cleaning path 160 is completed, then the cart 100 may advance to another position between two rows 128 to repeat the process and sanitize the surfaces along another segment of the cleaning path 160.

FIG. 23 depicts the trunk 134 of the UV light sanitizing cart 100 according to an alternative example. In the illustrated example, the trunk 134 is segmented to provide multiple articulation points 350 between trunk members 352. Actuators along the trunk 134 can enable pivoting of the trunk members 352 relative to each other at the articulation points 350, which can selectively position the carrier 214 at various different positions in space. The example shown in FIG. 23 can be used in conjunction with, or instead of, the base 132 shown in FIG. 22.

Referring to FIGS. 1-23, in at least one example, the UV light array 138 is configured to emit sanitizing UV light (through operation of the UV lamps 140) within a far UV spectrum, such as between 200 to 230. In at least one example, the UV light array 138 emits sanitizing UV light having a wavelength of 222. Optionally, the UV light array 138 is configured to emit sanitizing UV light at wavelengths other than within the far UV spectrum. For example, the UV light array 138 can emit sanitizing UV light within the UVC spectrum.

In one or more examples, the control unit 190 controls and/or directs the movement of the UV light array 138 (and/or a wand assembly of the UV light sanitizing cart 100) relative to the surfaces being sanitized to ensure that a designated or predetermined dosage of UV light is consistently administered to the surfaces along the cleaning paths 160, 180. The dosage is based on the power output or amplitude of the UV light that is emitted by the UV lamps 140, the proximity or range from the UV lamps 140 to the sanitizing surfaces, and the exposure or dwell time. The exposure time represents the length of time at which a given area is illuminated by the UV light as the UV light array 138 of the cart 100 sweeps the sanitizing surfaces. The designated dosage may be pre-selected based on operator preference, regulatory requirements, or the like. The power output or amplitude of the UV light may be set based on capability limits of the UV lamps 140 and/or desired energy consumption limits. The proximity distance may be selected to be within a few inches, such as 2 inches, 3 inches, 4 inches, or the like. These properties for the designated dosage, power, and proximity may be stored in the memory 199 and accessed by the one or more processors 197. Optionally, some of the properties may vary based on the type of surface being sanitized, so the memory 199 may store multiple values of some of the properties. In an example, based on the stored properties, the processor(s) can calculate a dwell time that represents the least amount of exposure time necessary to achieve the designated dosage on a given area of the sanitizing surfaces. The processor(s) can use the dwell time to determine a pacing speed of the UV light array 138 relative to the sanitizing surfaces for consistently achieving the designated dosage without unduly slowing the completion of the sanitizing task. The pacing speed indicates the correct speed for proper sanitization of the surfaces at the detected proximity distance, for the particular UV light and emitted power output of UV light.

The pacing speed can be stored in the memory 199 and used by the control unit 190 to control the movement of the UV light array 138 when tracing the contours of the surfaces. For example, as the UV light array 138 traces the surfaces, the control unit 190 receives and analyzes feedback from the sensors 194 and the actuators 196. The control unit 190 can receive proximity data from sensors 194 disposed on the arms 136 that measure the actual distance or range from the UV lamps 140 to the sanitizing surfaces in the cabin 102. Based on the proximity data, the control unit 190 can determine whether the UV light array 138 is maintaining the designated proximity to the surfaces (e.g., whether the array 138 is on course along the respective cleaning path 160, 180). Furthermore, the control unit 190 can determine the actual speed of the UV light array 138 relative to the surfaces and can compare the actual speed to the pacing speed stored in the memory 199. The actual speed may be determined based on feedback from the actuators 196. For example, the motion of the mechanical drive trains and motors may be converted by the control unit 190 to physical movement of the UV light array 138 in space, which when divided by time provides the actual speed. In another example, one or more of the sensors 194 may be used to track the movement of the UV light array 138 over time to determine the actual speed of the UV light array 138.

In an example, if the actual speed of the UV light array 138 differs from the pacing speed by more than a designated tolerance range (e.g., 2%, 5% or the like), then the control unit 190 can generate a control signal to modify the movement of the UV light array 138 relative to the surfaces to reduce the disparity between the actual speed and the pacing speed. The control signal can be communicated to one or more of the actuators 194 that can adjust the speed at which the actuators 194 operate based on the control signal. For example, if the actual speed is faster than the pacing speed, the dosage of UV light that is supplied may be insufficient to provide the desired level or amount of sanitization. In response, the control unit 190 generates a control signal to slow the movement of the UV light array 138 to increase the dosage. Conversely, if the actual speed is slower than the pacing speed, the dosage of UV light supplied to the surfaces may be more than sufficient to provide the desired level of sanitization, such that there is an opportunity to increase the energy efficiency and decrease the total cleaning time of the sanitization task by increasing the speed of the UV light array 138.

In the semi-autonomous mode, the speed of the UV light array 138 may be controlled in part by the operator pushing or pulling the cart 100 along the aisle 126. Upon determining the disparity between the actual speed and the pacing speed, the control unit 190 may generate a control signal to the output device 198. For example, if the actual speed is faster than the pacing speed, the control signal that is generated causes the output device 198 to alert or notify the operator that the speed is too fast and suggest slowing the movement of the cart 100. The alert may indicate the excessive speed through corresponding lighting effects (e.g., emitting red light, blinking lights, or the like), audio effects (e.g., frequent, high frequency, and/or loud beeps), and/or tactile effects (e.g., vibration of the handle 146) provided by the output device(s) 198. In another example, if the actual speed is slower than the pacing speed, the control signal may cause the output device 198 to provide different corresponding lighting and/or audio effects, such as a yellow light, to indicate to the operator that the operator could increase the speed of the cart 100. If the actual speed is within the tolerance range of the pacing speed, the control signal may cause the output device 198 to provide another corresponding lighting and/or audio effect, such as a green light, or may not provide any lighting and/or audio effect.

As the arms 136 and other movable components of the UV light sanitizing cart 100 are actuated to control the UV light array 138 to follow the cleaning paths 160, 180 along the contours of the surfaces in the cabin 102 as shown in FIG. 4, the speed of the cart 100 along the aisle 126 will vary. In one or more examples in which the rolling movement of the base 132 along the aisle 126 is used to move the UV light array 138 along the longitudinal axis, the control unit 190 may automatically control the direction and speed of movement of the base 132 and wheels 142 according to the surface being sanitized. For example, as the UV light array 138 sanitizes the floor 114 between rows of seats 120 or the ceiling 116, the base 132 may move as a relatively constant speed based on the determined dwell time. But, as the UV light array 138 is moved essentially vertically to sanitize the back of the seat back of a seat 120, for example, the base 132 is controlled to remain stationary until longitudinal movement of the UV light array 138 is again desired. Based on the contours of the surfaces the base 132 may even move in the reverse direction that is opposite the general direction of the cleaning path, at least temporarily to enable the UV light array 138 to keep hugging the contours and avoid making direct contact with any objects in the cabin 102.

In the examples shown in FIGS. 22 and 23 in which the UV light array 138 can be moved longitudinally relative to the base 132, the base 132 may be controlled via the control unit 190 and/or an operator to sequentially move and then pause at various locations along the length of the aisle 126. For example, the cart 100 may be moved or driven to a position that aligns with a row 128 or between two rows 128. Then, the base 132 of the cart 100 remains stationary while the trunk 134, carrier 214, and/or arms 136 manipulate the UV light array 138 to follow the contours of the surface along the row or the two rows. The base 132 can remain stationary because the longitudinal movements of the UV light array 138 can be accomplished by moving the trunk 134 as shown in FIG. 22 and/or FIG. 23. Upon completion of the sanitizing of the row or the two rows, the base 132 is then controlled to advance to another position along the aisle 126 to repeat the process.

In an alternative example, the UV light sanitizing cart 100 may include additional UV lamps 140 that are selective extendable from the arms 136. The additional UV lamps 140 may be disposed on end effectors that are mounted to the arms 136 and selectively project from the arms 136. For example, the end effectors may selectively pivot out of the plane of the arms 136 to position the respective UV lamp 140 in front of or rearward of the arms 136 (e.g., along the longitudinal axis). The UV lamps 140 on the end effectors can be oriented at angles up to 90 degrees relative to the UV lamps 140 on the arms 136, thereby providing an L or T-shaped UV array at the end effectors. The UV lamps 140 on the end effectors can be used to sanitize within cavities and underneath objects, such as underneath the passenger seats 120. For example, although the arms 136 that extend laterally across the seats 120 may not be able to get close enough to the area underneath the seats, the end effector can project from the arms 136 into the space that is immediately under the seat bottoms to sanitize the floor 114 under the seats 120 and/or the bottom surfaces of the seat bottoms. The UV lamps 140 on the end effectors can also be used to sanitize armrests, portions of the storage bins, walls, and/or the like. The numerous axes of translation and rotation provided by the cart 100 enables positioning and aiming the UV lamps 140 to essentially duplicate the capabilities of a person holding a UV light wand, without the inherent inconsistencies in speed, coverage area, and proximity associated with manual sanitization.

In at least one embodiment, the UV light sanitizing cart 100 includes a wand assembly, such as a handheld UV wand, that is coupled to the cart 100. The wand assembly provides the option for a person to utilize the wand in conjunction with the automated sanitization by the cart 100 to either sanitize areas that are difficult for the cart 100 to access or to provide additional UV dosage to certain high traffic areas. The wand can be tethered to the cart 100 by at least a power cable to power the UV lamp on the wand. Alternatively, the wand can be battery powered. Optionally, the wand can include light sensors that indicate to the operator whether the UV lamp is disposed at a desired proximity distance (or range) from the surface being sanitized. The light sensors that indicate the range of the wand from the surface are disclosed in U.S. Provisional Application No. 63/027,869.

In one or more examples, an ultraviolet (UV) light sanitizing cart is provided that includes a UV light array, a body, actuators, and a control unit. The UV light array includes UV lamps configured to emit UV light to sanitize a surface of a component. The body includes a mobile base and multiple interconnected rigid members supported by the base. The UV lamps are mounted to at least one of the rigid members. The actuators are mechanically connected to the body. At least some of the actuators are configured to control movement of the rigid members relative to one another and to the base. The control unit is configured to generate control signals for controlling the actuators to cause the UV light array to move along a cleaning path that follows a contour of the surface.

Optionally, the rigid members include arms and a trunk. The trunk is mounted to the mobile base. The arms extend from the trunk in opposite directions and hold at least some of the UV lamps to provide a linear arrangement of the UV lamps. Each of the arms may include at least an inner member and an outer member. The inner member is disposed between the outer member and the trunk. The outer member is configured to retract to nest within the inner member and to linearly extend outward from the inner member to increase the length of the arm. Optionally, at least some of the actuators are connected to the arms and are controllable by the control unit to pivot the arms to a collapsed state in which the arms are parallel to and adjacent the trunk.

Optionally, the UV light array includes a linear arrangement of multiple UV lamps that extends along an array axis. The actuators and the body are configured to translate the UV light array along two axes perpendicular to each other and to the array axis, and are configured to rotate the UV light array about the array axis.

Optionally, the mobile base includes multiple wheels that interface with a floor and support the cart. The actuators include motors onboard the mobile base for driving rotation of the wheels and steering the wheels. The control signals that are generated by the control unit to cause the UV light array to move along the cleaning path may include control signals to the motors onboard the mobile base for driving the mobile base along a cart path to translate the UV light array along an axis parallel to the cart path.

Optionally, the body includes a retractable handle configured to be held by an operator that manually propels the cart along a cart path to translate the UV light array along an axis parallel to the cart path.

Optionally, the cart further includes sensors mounted on the body and configured to generate sensor data indicative of a proximity of the cart to the surface of the component or to a surface of another component. The control unit is configured to generate the control signals based on the sensor data to avoid a collision between the cart and the surface of the component or the surface of the other component.

Optionally, the control unit includes a memory device that stores a three-dimensional map of an environment in which the component is located. The control unit is configured to determine a reference location of the UV light array relative to the three-dimensional map and to generate the control signals to cause the UV light array to move along the cleaning path in the environment based on the three-dimensional map and the reference location of the UV light array.

Optionally, the cart further includes sensors mounted on the rigid members of the body proximate to the UV lamps. The sensors are configured to generate sensor data indicative of a proximity of the UV lamps to the surface of the component. The control unit is configured to generate the control signals based on the sensor data to maintain the UV lamps at a designated proximity distance from the surface to ensure that a designated dosage of UV light is applied to the surface.

Optionally, the control unit includes a memory device that stores a pacing speed for the UV light array. The pacing speed is based on a power output of the UV lamps and a designated proximity distance between the UV lamps and the surface of the component to provide a designated dosage of UV light to the surface. The control unit is configured to generate the control signals to control the actuators to cause the UV light array to move along the cleaning path at a rate based on the pacing speed. The control unit may be configured to determine an actual speed of the UV light array relative to the surface of the component and to compare the actual speed to the pacing speed. Responsive to the actual speed being greater than the pacing speed, the control unit may be configured to generate control signals to control the actuators to slow the movement of the UV light array along the cleaning path.

Optionally, the control unit includes a memory device and the control unit is configured to store in the memory device a record of sanitization tasks performed by the cart over time.

Optionally, the control unit is configured to generate the control signals for at least two actuators of the actuators to provide compound movements of the UV light array such that the UV light array one or more of (i) concurrently rotates about two different axes, (ii) concurrently translates along two different axes, or (iii) concurrently rotates about one axis and translates about the one axis or a different axis.

In one or more examples, a method is provided that includes providing a cart including a body that holds an ultraviolet (UV) light array. The UV light array includes UV lamps configured to emit UV light to sanitize a surface of a component. The cart further includes actuators mechanically connected to the body and a control unit communicatively connected to the actuators. The method includes determining, via the control unit, a cleaning path for the UV light array that follows a contour of the surface and generating control signals, via the control unit, to control the actuators to move the body such that the UV light array follows the cleaning path.

Optionally, the UV light array includes a linear arrangement of multiple UV lamps that extends along an array axis. The control signals may be generated to control the actuators and the body to translate the UV light array along two axes perpendicular to each other and to the array axis, and to rotate the UV light array about the array axis as the UV light array follows the cleaning path.

Optionally, the body includes a mobile base having multiple wheels that support the base and the actuators include one or more motors onboard the base for driving rotation of the wheels and steering the wheels. Generating the control signals may include generating control signals for driving the mobile base along a cart path to translate the UV light array along an axis parallel to the cart path.

Optionally, the method further includes receiving sensor data indicative of a proximity of the UV light array to the surface of the component. The control signals are generated based on the sensor data to one or more of (i) avoid a collision between the cart and the surface of the component or (ii) maintain a designated proximity distance between the UV lamps and the surface of the component to provide a designated dosage of UV light to the surface.

Optionally, the method further includes storing a pacing speed for the UV light array in a memory device. The pacing speed may be based on a power output of the UV lamps and a designated proximity distance between the UV lamps and the surface of the component to provide a designated dosage of UV light to the surface. The method may also include determining, via the control unit, an actual speed of the UV light array relative to the surface of the component, and generating control signals to control the actuators to change the actual speed of the UV light array along the cleaning path responsive to the actual speed differing from the pacing speed by more than a designated tolerance range.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms.

The control unit 190 is configured to execute a set of instructions that are stored in one or more data storage units or elements (such as one or more memories 199), in order to process data. The data storage units may also store data or other information as desired or needed. The data storage units may be in the form of an information source or a physical memory element within a processing machine.

The set of instructions may include various commands that instruct the control unit 190 as a processing machine to perform specific operations such as the methods and processes of the various examples of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of examples herein may illustrate one or more control or processing units, such as the control unit 190. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 190 may represent processing circuitry such as one or more of a field programmable gate array (FPGA), application specific integrated circuit (ASIC), microprocessor(s), and/or the like. The circuits in various examples may be configured to execute one or more algorithms to perform functions described herein. The one or more algorithms may include aspects of examples disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Certain examples of the subject disclosure provide systems and methods to autonomously control UV lamps to follow contours of surfaces to provide consistent, efficient, and effective sanitization of the surfaces. The automated control of the UV lamps ensure that a correct dosage of UV light is delivered to the surfaces to effectively sanitize the surface. The UV light sanitizing cart described herein is collapsible and stowable onboard a vehicle, such that the cart can be operated when desired and then stowed away when not desired, such as during a trip of the vehicle.

Figure 24:
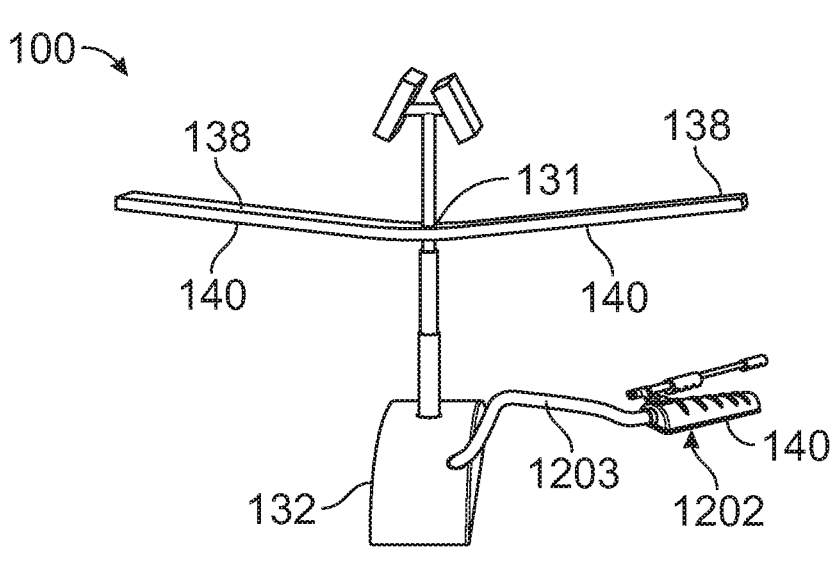
FIG. 24 illustrates a perspective front view the UV light sanitizing cart, according to an example of the subject disclosure.

FIG. 24 illustrates a perspective front view the UV light sanitizing system or cart 100, according to an example of the subject disclosure. As described herein, the UV light sanitizing cart 100 includes the body 131 having the mobile base 132, and the UV light array 138 including UV lamps 140 configured to emit UV light to sanitize a surface of a component. The UV light sanitizing cart 100 also includes a wand assembly 1202. In at least one embodiment, the wand assembly 1202 is coupled to the body 131. For example, the wand assembly 1202 is coupled to the base 132. The wand assembly 1202 is configured to be selectively moved between a stowed position, such as on the base 132, and a deployed position, in which the wand assembly 1202 is moved away from the base 132. In the deployed position, the wand assembly 1202 can be connected to the base 132 through a tether 1203, which can include a power cord, cable, air hose, and/or the like.

In at least one embodiment, the UV light array 138 of the UV light sanitizing cart 100 is configured to emit UV light at a particular wavelength, such as within the far UV light spectrum, or the UVC spectrum, and the UV lamp of the wand assembly 1202 is configured to emit UV light at a particular wavelength, which may be the same or different from that of the UV light emitted by the UV light array 138 of the UV light sanitizing cart 100. As an example, the UV light array 138 can emit UV light at a first wavelength, such as within the far UV light spectrum or the UVC spectrum, and the UV lamp of the wand assembly 1202 can emit UV light at a second wavelength that differs from the first wavelength, such as within the far UV light spectrum or the UVC spectrum.

In at least one other example, the UV light sanitizing cart 100 can be a galley cart having one or more UV light sources, such as one or more UV lamps 140. The wand assembly 1202 can be coupled to the galley cart.

In at least one example, the wand assembly 1202 is attached to the body 131 through the tether 1203, which includes a power cord and/or a cooling air hose. The wand assembly 1202 receives power from one or more power sources of the UV sanitation cart 100, as described herein. The wand assembly 1202 includes a UV lamp 140 that is configured to emit UV light in any germicidal UV band, such as between 200 to 320. In at least one example, the UV lamp 140 of the wand assembly 1202 is configured to emit UV light in the far UV spectrum, such as between 200 to 230, which has been found to be safe for humans.

The UV wand assembly 1202 allows an individual to disinfect surfaces of components that may be shadowed, or likely to be insufficiently disinfected by the UV light array 138. For example, the wand assembly 1202 can be moved from a stowed position on the body 131 and moved and oriented in relation to surfaces that may be shadowed.

As described herein, examples of the subject disclosure provide the UV light sanitizing cart 100 including one more first UV lamps 140 configured to emit UV light, and the wand assembly 1202 including one or more second UV lamps 140 configured to emit UV light. In at least one embodiment, the UV light array 138 includes the first UV lamp(s) 140. As another example, the UV light sanitizing cart 100 can be a galley cart that includes the first UV lamp(s) 140 secured on or within portions thereof.

Optionally, the UV light sanitizing cart 100 can be sized, shaped, and configured differently than shown. In at least one example, the UV light sanitizing cart 100 is or is otherwise sized and shaped as a galley cart. In at least one example, the UV light sanitizing cart 100 includes UV light sources, such as one or more UV lamps, secured to outer portions thereof, whether part of moveable arrays or not. In at least one other example, the cart portion may not include UV light sources. Instead, the UV light sanitizing cart 100 can include the wand assembly 1202 having one or more UV lamps coupled to a moveable cart (whether configured as shown in FIG. 24 or differently) that may or may not include additional UV light sources.

Figure 25:
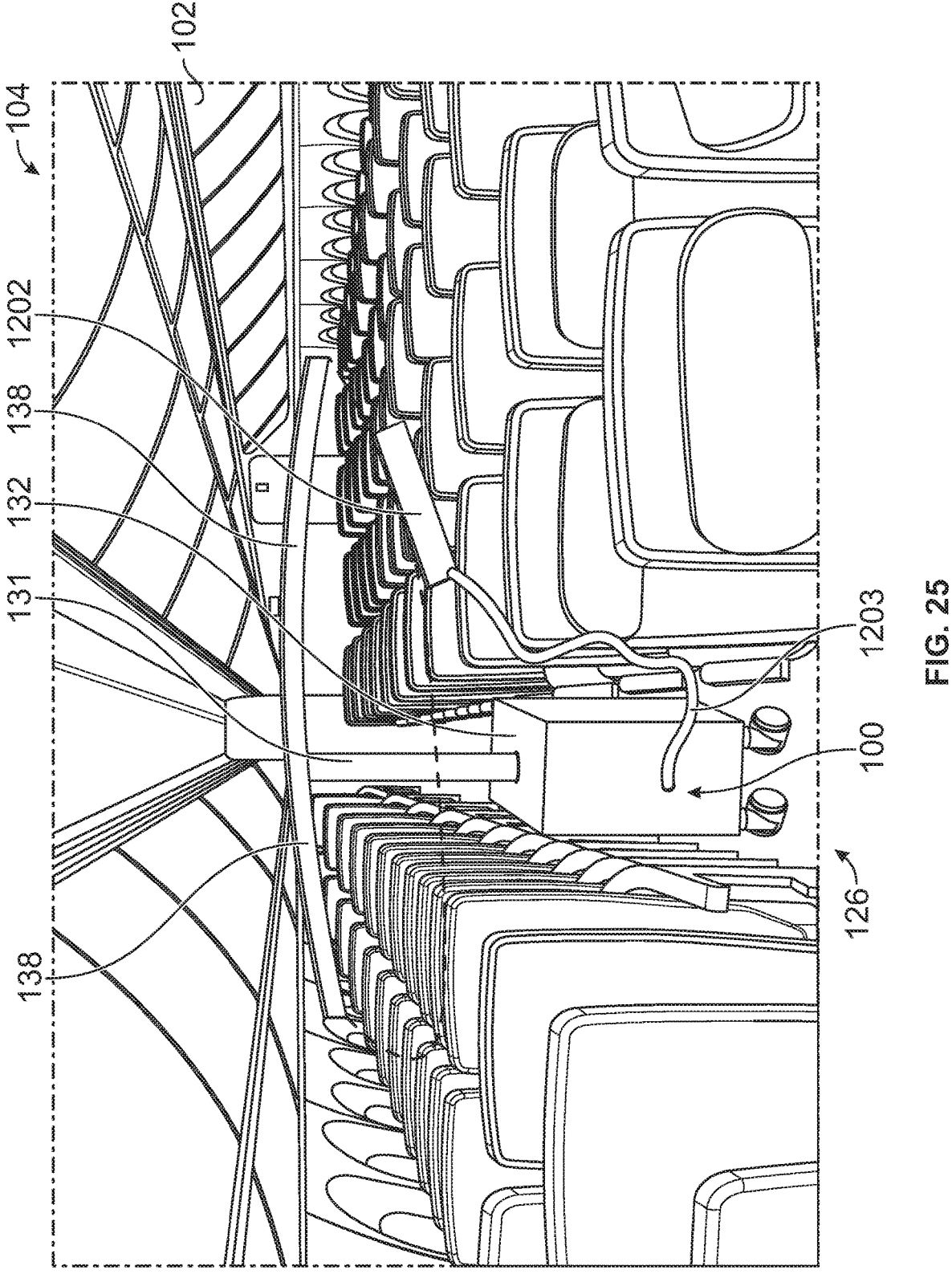
FIG. 25 illustrates a perspective view of the UV light sanitizing cart within an internal cabin of a vehicle, according to an example of the subject disclosure.

FIG. 25 illustrates a perspective view of the UV light sanitizing cart 100 within the internal cabin 102 of the vehicle 104, according to an example of the subject disclosure. The UV light sanitizing cart 100 is configured to be moved through the aisle 126, as described herein. The wand assembly 1202 is shown in the deployed position in FIG. 25. The wand assembly 1202 is moved by an individual to emit sanitizing UV light, via the UV lamp 140 of the wand assembly 1202, to sanitize surfaces of components that may be shadowed. For example, the shadowed surfaces may not receive UV light from the UV light array 138 of the UV light sanitizing cart 100. As such, the wand assembly 1202 is moved to areas that may otherwise not be sufficiently exposed to the UV light emitted from the UV light array 138.

Figure 26:
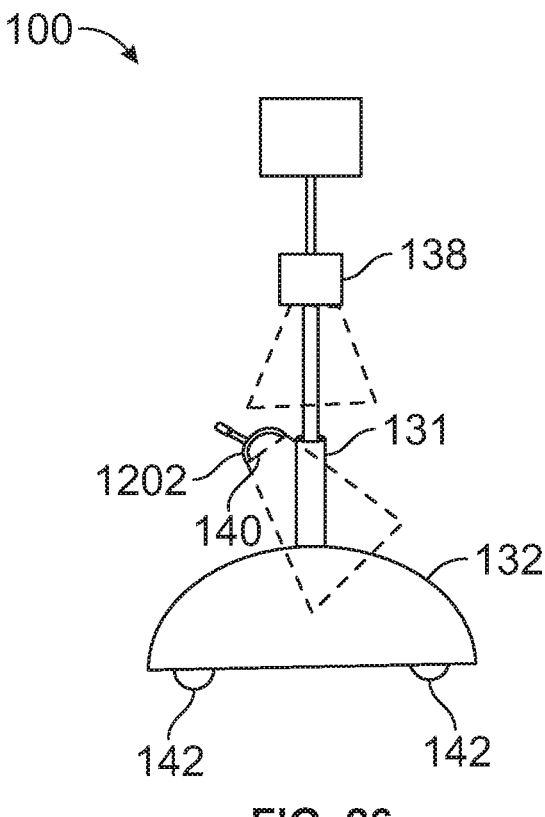
FIG. 26 illustrates a lateral view of the UV light sanitizing cart of FIG. 24.

FIG. 26 illustrates a lateral view of the UV light sanitizing cart 100 of FIG. 24. The wand assembly 1202 can be moved and maneuvered in various different orientations. For example, the wand assembly 1202 can be moved away from the body 131 toward and proximate to components, such as between seats within an internal cabin. The wand assembly 1202 can be extended, rotated, angled, or the like to reach areas that may otherwise not be readily reached by the UV light array 138.

The wand assembly 1202 provides increased versatility to the UV light sanitizing cart 100. The wand assembly 1202 is able to reach tighter spaces as compared to the UV light array 138. The wand assembly 1202 is able to be moved closer to certain components (such as tray tables, between seats, walls portions, or the like) within an internal cabin as compared to the UV light array 138. The UV lamp 140 of the wand assembly 1202 is able to emit sanitizing UV light onto surfaces that are likely to be shadowed by other components and/or the UV light sanitizing cart 100 itself.

Figure 27:
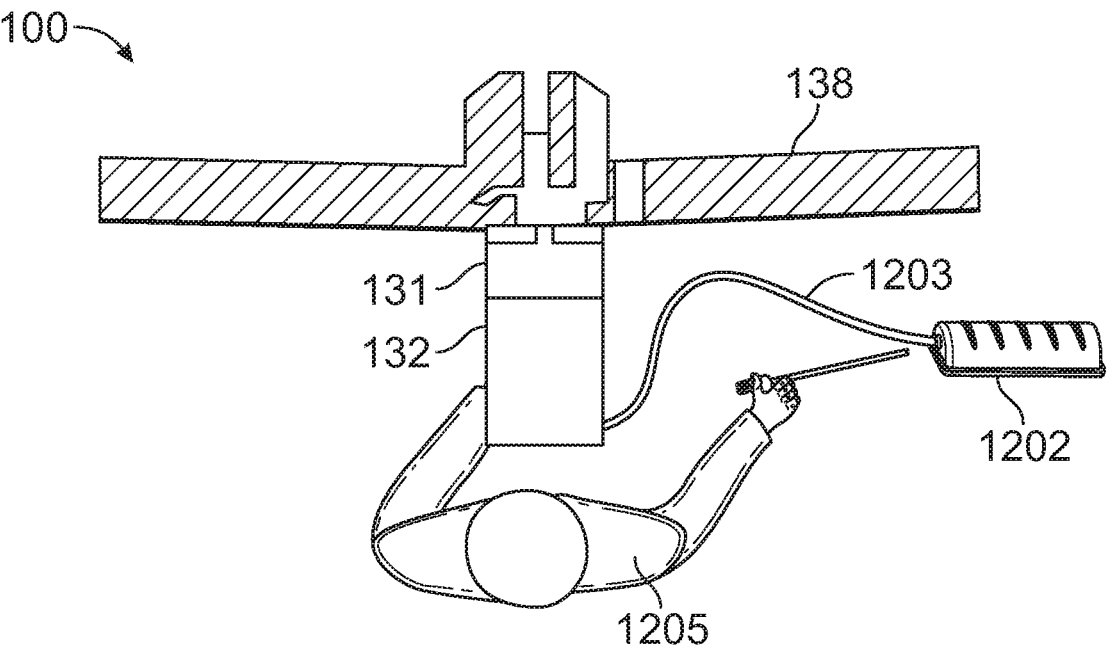
FIG. 27 illustrates a top view of the UV light sanitizing cart of FIG. 24.

FIG. 27 illustrates a top view of the UV light sanitizing cart 100 of FIG. 24. As shown, an individual 1205 can move the wand assembly 1202 into a deployed position, in which the wand assembly 1202 can be moved relative to the body 131.

As shown, the wand assembly 1202 is connected to the body 131 through the tether 1203, which can include one or more power cables, an air hose, and/or the like. In at least one other example, the wand assembly 1202 is not connected to the body 131 through the tether 1203. Instead, the wand assembly 1202 can be fully independent in relation to the body 131. In this example, the wand assembly 1202 can include its own power source, such as one or more batteries.

The individual 1205 moves the UV light sanitizing cart 100, such as by pushing the UV light sanitizing cart 100 within an aisle of an internal cabin, as described herein. Optionally, the UV light sanitizing cart 100 can include one or more actuators, motors, or the like that allow the UV light sanitizing cart 100 to automatically move within an environment. That is, the UV light sanitizing cart 100 can be moved by an individual or autonomously move.

Figure 28:
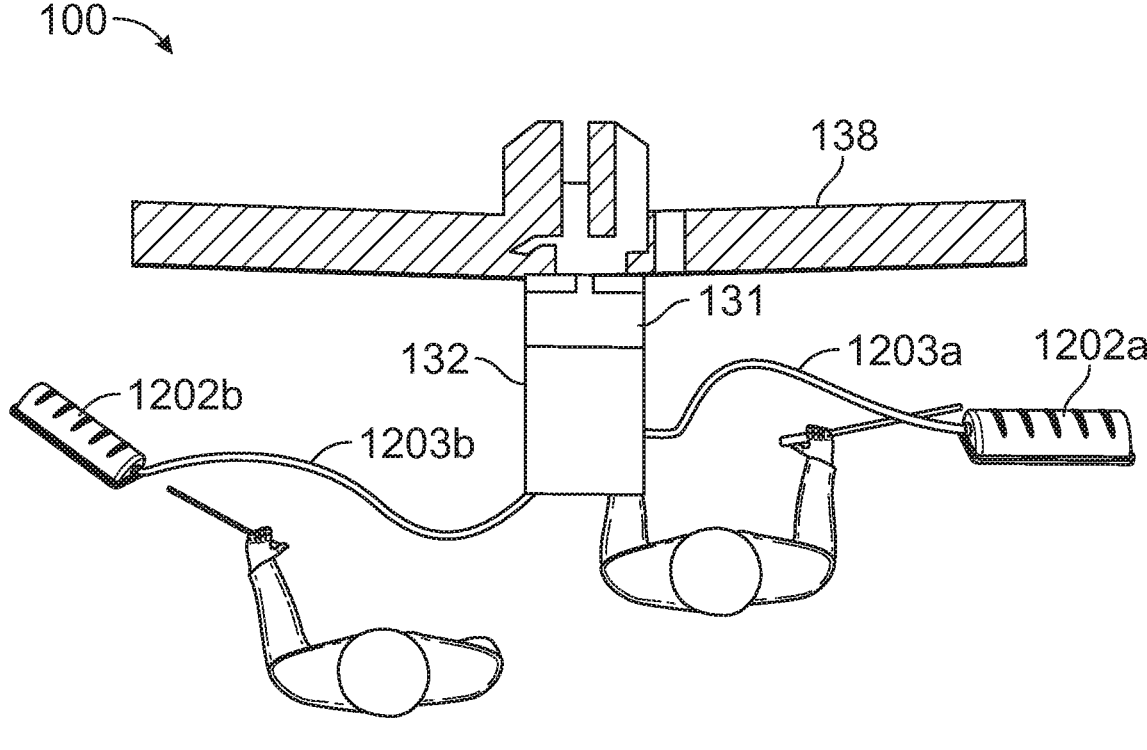
FIG. 28 illustrates a top view of the UV light sanitizing cart, according to an example of the subject disclosure.

FIG. 28 illustrates a top view of the UV light sanitizing cart 100, according to an example of the subject disclosure. In at least one example, the UV light sanitizing cart 100 includes a first wand assembly 1202a coupled to the body 131 through a first tether 1203a, and a second wand assembly 1202b coupled to the body 131 through a second tether 1203b.

Figure 29:
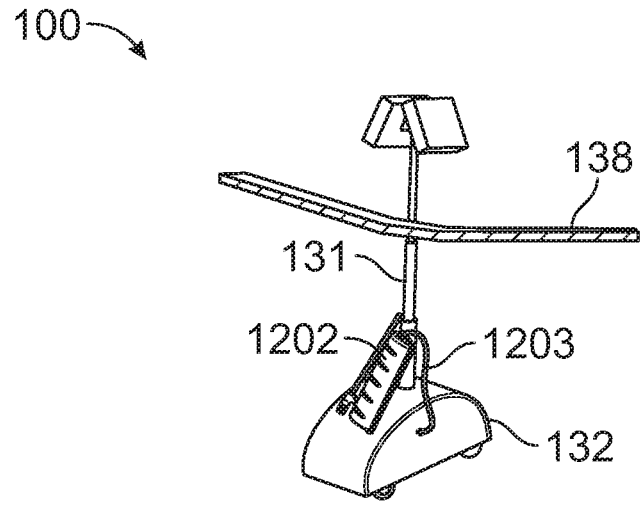
FIG. 29 illustrates a perspective front view of the UV light sanitizing cart having a wand assembly in a stowed position, according to an example of the subject disclosure.

FIG. 29 illustrates a perspective front view of the UV light sanitizing cart 100 having the wand assembly 1202 in a stowed position, according to an example of the subject disclosure. For example, the wand assembly 1202 can be removably secured to a portion of the body 131, such as the base 132, through one or more clips, latches, snaps, ties, or the like. In at least one example, the base 132 includes a recess that conforms to an outer surface of at least a portion of the wand assembly 1202. The wand assembly 1202 is retained within the recess. As another example, the wand assembly 1202 in the stowed position can be secured to the base 132 through an interference fit. As another example, the body 131 includes an internal compartment that is covered by a moveable door. The wand assembly 1202 can be stowed within the internal compartment when not in use.

Figure 30:
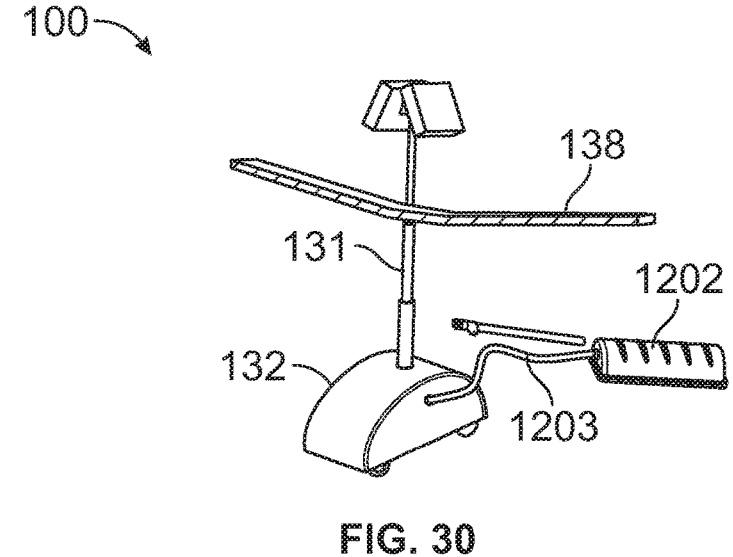
FIG. 30 illustrates a perspective front view of the UV light sanitizing cart having the wand assembly in a deployed position, according to an example of the subject disclosure.

FIG. 30 illustrates a perspective front view of the UV light sanitizing cart 100 having the wand assembly 1202 in a deployed position, according to an example of the subject disclosure. An individual moves the wand assembly 1202 from the stowed position into the deployed position, as desired, and moves the wand assembly 1202 to areas that may otherwise not be easily reached by the UV light array 138.

Figure 31:
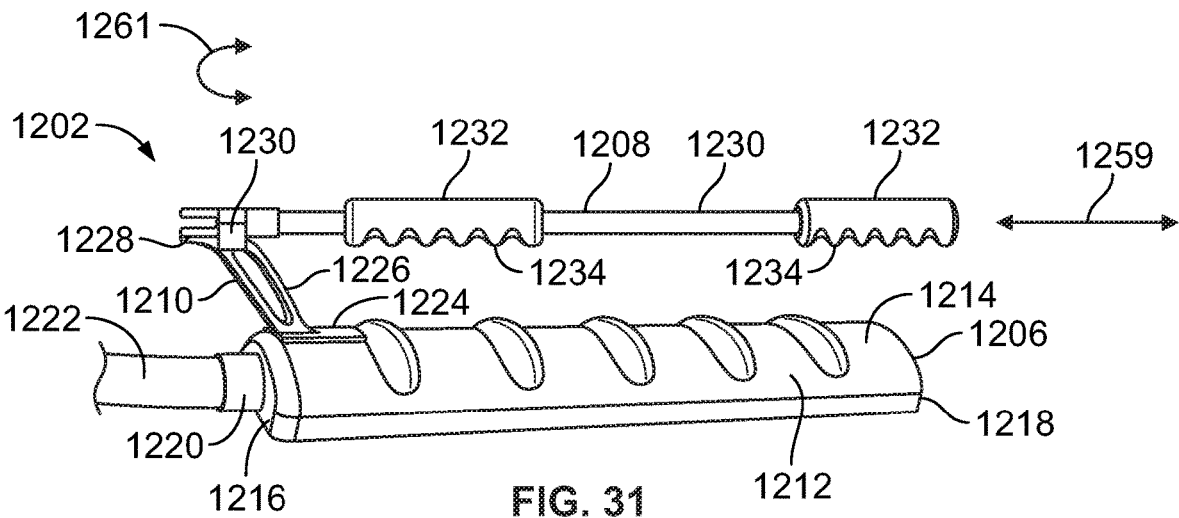
FIG. 31 illustrates a perspective lateral top view of the wand assembly, according to an example of the subject disclosure.

FIG. 31 illustrates a perspective lateral top view of the wand assembly 1202, according to an example of the subject disclosure. The wand assembly 1202 includes a sanitizing head 1206 coupled to a handle 1208. In at least one example, the sanitizing head 1206 is moveably coupled to the handle 1208 through a coupler 1210.

The sanitizing head 1206 includes a shroud 1212 having an outer cover 1214 that extends from a proximal end 1216 to a distal end 1218. As described herein, the shroud 1212 contains a UV light source, such as a UV lamp.

Optionally, the wand assembly 1202 can include the sanitizing head 1206 connected to a fixed handle. Further, the wand assembly 1202 can be sized and shaped differently than shown.

A port 1220 extends from the proximal end 1216. The port 1220 couples to a hose 1222, which, in turn, couples to a portion of the UV light sanitizing cart 100, such as a portion of the body 131 (as shown in FIGS. 24-30). The hose 1222 is an example of the tether 1203 shown in FIGS. 24-30. In at least one example, the hose 1222 contains electrical cords, cables, wiring, or the like that couples a power source or supply (such as one or more batteries) within the UV light sanitizing cart 100 to a UV lamp within the shroud 1212. Optionally, the electrical cords, cables, wiring, or the like may be outside of the hose 1222. In at least one embodiment, the hose 1222 also contains an air delivery line, such as an air tube) that fluidly couples an internal chamber of the shroud 1212 to an air blower, vacuum generator, air filters, and/or the like within the UV light sanitizing cart 100.

The coupler 210 is secured to the outer cover 1214 of the shroud 1212, such as proximate to the proximal end 1216. The coupler 1210 may include a securing beam 1224 secured to the outer cover 1214, such as through one or more fasteners, adhesives, and/or the like. An extension beam 1226 outwardly extends from the securing beam 1224, thereby spacing the handle 1208 from the shroud 1212. A bearing assembly 1228 extends from the extension beam 1226 opposite from the securing beam 1224. The bearing assembly 1228 includes one or more bearings, tracks, and/or the like, which allow the handle 1208 to linearly translate relative to the coupler 1210 in the directions of arrows 1259, and/or pivot about a pivot axle in the directions of arc 1261. Optionally, the securing beam 1224 may include a bearing assembly that allows the sanitizing head 1206 to translate in the directions of arrows A, and/or rotate (for example, swivel) in the directions of arc B in addition to, or in place of, the handle 1208 being coupled to the bearing assembly 1228 (for example, the handle 1208 may be fixed to the coupler 1210).

In at least one other example, the wand assembly 1202 does not include the coupler 1210. Instead, the handle 1208 may be fixed to the shroud 1212, for example.

In at least one example, the handle 1208 includes a rod, pole, beam, or the like 1230, which may be longer than the shroud 1212. Optionally, the rod 1230 may be shorter than the shroud 1212. One or more gripsl 232 are secured to the rod 1230. The grips 1232 are configured to be grasped and held by an individual. The grips 1232 may include ergonomic tactile features 1234.

Figure 32:
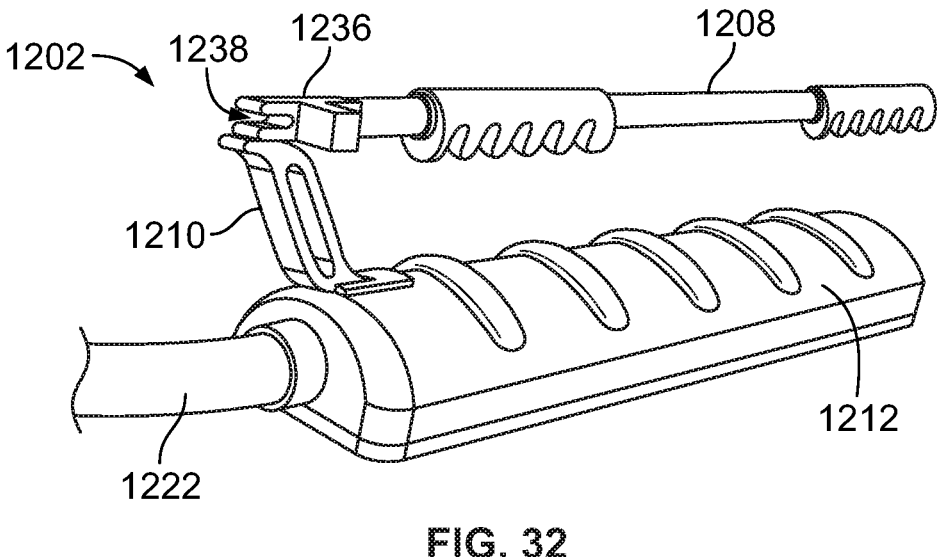
FIG. 32 illustrates a perspective rear view of the wand assembly of FIG. 31.
Figure 33:
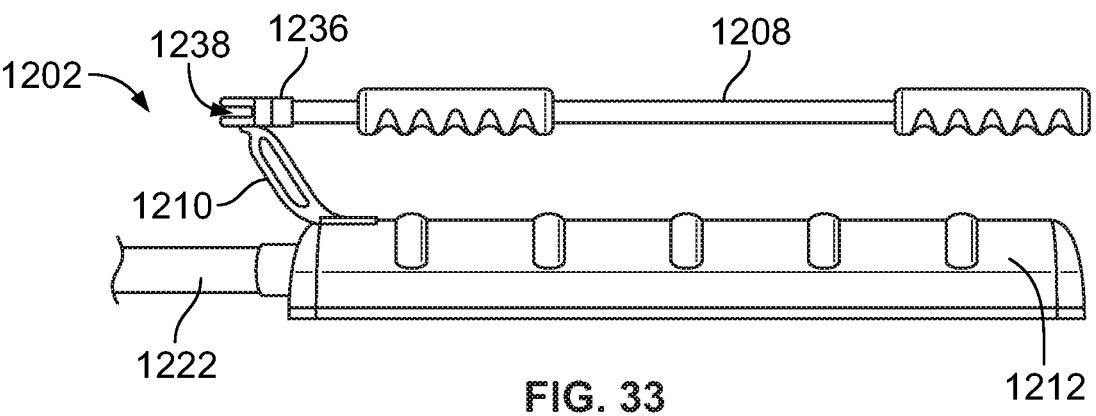
FIG. 33 illustrates a perspective lateral view of the wand assembly of FIG. 31.

FIG. 32 illustrates a perspective rear view of the wand assembly 1202 of FIG. 31. FIG. 33 illustrates a perspective lateral view of the wand assembly 1202 of FIG. 31. Referring to FIGS. 32 and 33, the handle 1208 may pivotally couple to the coupler 1210 through a bearing 1236 having a pivot axle 1238 that pivotally couples the handle 1208 to the coupler 1210. The handle 1208 may further be configured to linearly translate into and out of the bearing 1236. For example, the handle 1208 may be configured to telescope in and out. Optionally, or alternatively, in at least one embodiment, the handle 1208 may include a telescoping body that allows the handle 1208 to outwardly extend and inwardly recede. In at least one other embodiment, the handle 1208 may not be configured to move, extend, retract, or the like relative to the shroud 1212.

In order to extend the sanitizing head 1206 relative to the handle 1208, the sanitizing head 1206 is outwardly slid relative to the handle 1208 (or the handle 1208 is rearwardly slid relative to the sanitizing head 1206). As noted, the sanitizing head 1206 is able to linearly translate relative to the handle 1208 via the coupler 1210. The outward extension of the sanitizing head 1206 allows for the wand assembly 1202 to easily reach distant areas. Alternatively, the sanitizing head 1206 may not linearly translate relative to the handle 1208.

To reach even further, the handle 1208 may be configured to linearly translate, such as through a telescoping portion, to allow the sanitizing head 1206 to reach further outwardly. Alternatively, the handle 1208 may not be configured to extend and retract.

In at least one embodiment, the handle 1208 may include a lock. The lock is configured to be selectively operated to secure the handle 1208 into a desired extended (or retracted) position.

As noted, the sanitizing head 1206 is configured to rotate relative to the handle 1208 via the coupler 1210. Rotating the sanitizing head 1206 relative to the handle 1208 allows the sanitizing head 1206 to be moved to a desired position, and sweep or otherwise reach into areas that would otherwise be difficult to reach if the sanitizing head 1206 was rigidly fixed to the handle 1208. Alternatively, the sanitizing head 1206 may not be rotatable relative to the handle 1208.

Figure 34:
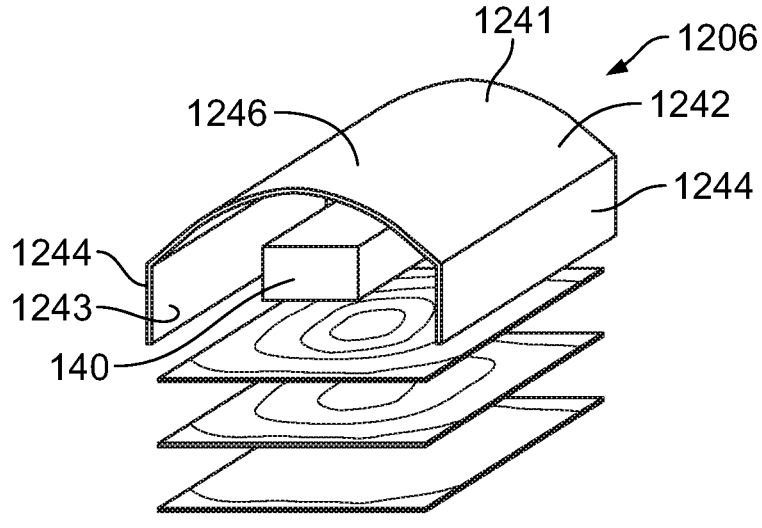
FIG. 34 illustrates a perspective end view of a UV lamp and a reflector of the sanitizing head, according to an example of the subject disclosure.

FIG. 34 illustrates a perspective end view of a UV lamp 140 and a reflector 1242 of the sanitizing head 1206, according to an example of the subject disclosure. The UV lamp 140 and the reflector 1242 are secured within the shroud 1212 (shown in FIG. 31, for example) of the sanitizing head 1206. In at least one embodiment, the reflector 1242 is secured to an underside 1241 of the shroud 1212, such as through one or more adhesives. As another example, the reflector 1242 is an integral part of the shroud 1212. For example, the reflector 1242 may be or otherwise provide the underside 1241 of the shroud 1212. The reflector 1242 provides a reflective surface 1243 (such as formed of Teflon, a mirrored surface, and/or the like) that is configured to outwardly reflect UV light emitted by the UV lamp 140. In at least one example, shroud 1212 may be or include a shell formed of fiberglass, and the reflector 1242 may be formed of Teflon that provides a 98% reflectivity. In at least one embodiment, the reflector 1242 may be a multi-piece reflector.

The reflector 1242 may extend along an entire length of the underside 1241 of the shroud 1212. Optionally, the reflector 1242 may extend along less than an entire length of the underside 1241 of the shroud 1212.

The UV lamp 140 may extend along an entire length (or along substantially the entire length, such as between the ends 1216 and 1218). The UV lamp 140 is secured to the reflector 1242 and/or the shroud 1212 through one or more mounts, such as brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200-230. In at least one embodiment, the UV lamp 140 is configured to emit UV light having a wavelength of 222. For example, the UV lamp 140 may be or include a 300 W bulb that is configured to emit UV light having a wavelength of 222. Alternatively, the UV lamp 140 may be configured to emit UV light in other portions of the UV spectrum, such as the UVC spectrum.

As shown, the reflector 1242 includes flat, upright side walls 1244 connected together through an upper curved wall 1246. The upper curved wall 1246 may be bowed outwardly away from the UV lamp 140. For example, the upper curved wall 1246 may have a parabolic cross-section and/or profile.

It has been found that the straight, linear side walls 1244 provide desired reflection and/or focusing of UV light emitted from the UV lamp 1240 toward and onto a desired location. Alternatively, the side walls 1244 may not be linear and flat.

Figure 35:
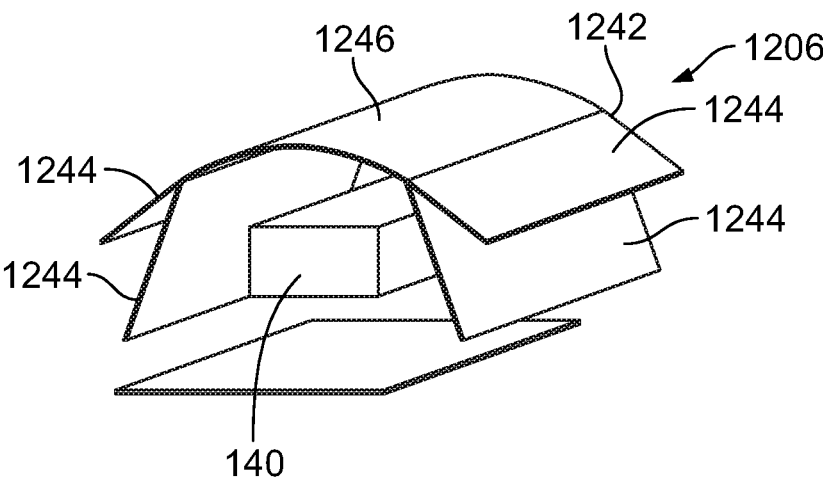
FIG. 35 illustrates a perspective end view of a UV lamp and a reflector of the sanitizing head, according to an example of the subject disclosure.

FIG. 35 illustrates a perspective end view of the UV lamp 140 and a reflector 1242 of the sanitizing head 1206, according to an example of the subject disclosure. The reflector 1242 shown in FIG. 35 is similar to the reflector 1242 shown in FIG. 34, except that the side walls 1244 may outwardly cant from the upper curved wall 1246.

Figure 36:
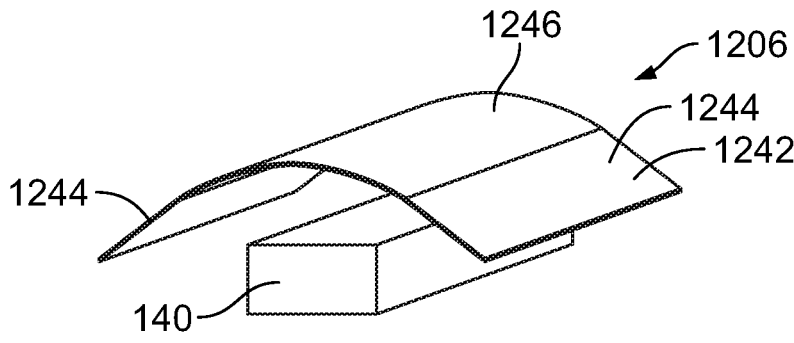
FIG. 36 illustrates a perspective end view of a UV lamp and a reflector of the sanitizing head, according to an example of the subject disclosure.

FIG. 36 illustrates a perspective end view of the UV lamp 140 and the reflector 1242 of the sanitizing head 1206, according to an example of the subject disclosure. In this embodiment, the side walls 1244 may be curved according to the curvature of the upper curved wall 1246.

Figure 37:
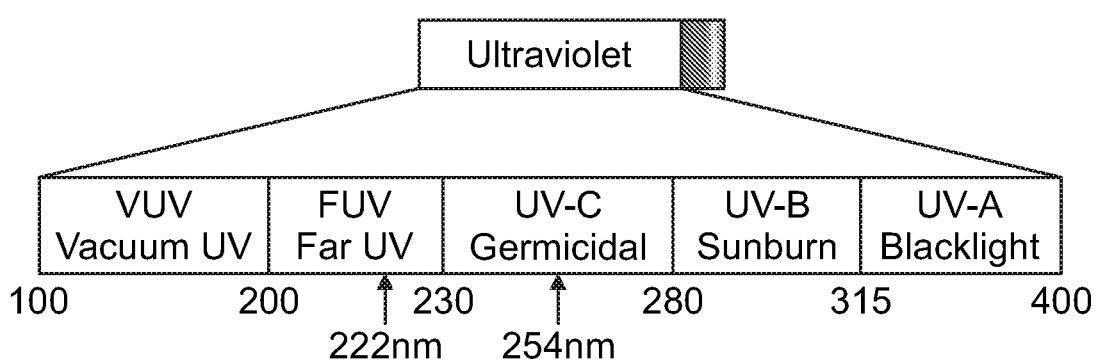
FIG. 37 illustrates an ultraviolet light spectrum.

FIG. 37 illustrates an ultraviolet light spectrum. Referring to FIGS. 1-37, in at least one example, the UV lamps, such as those of the UV light array 138 and the wand assembly 1202, are configured to emit sanitizing UV light within a far UV spectrum, such as between 200 to 230. In at least one embodiment, the UV lamps emit sanitizing UV light having a wavelength of 222.

Optionally, the UV lamps can be configured to emit UV light at wavelengths other than between 200-230. For example, the UV lamps can emit UV light within the UVC spectrum.

Figure 38:
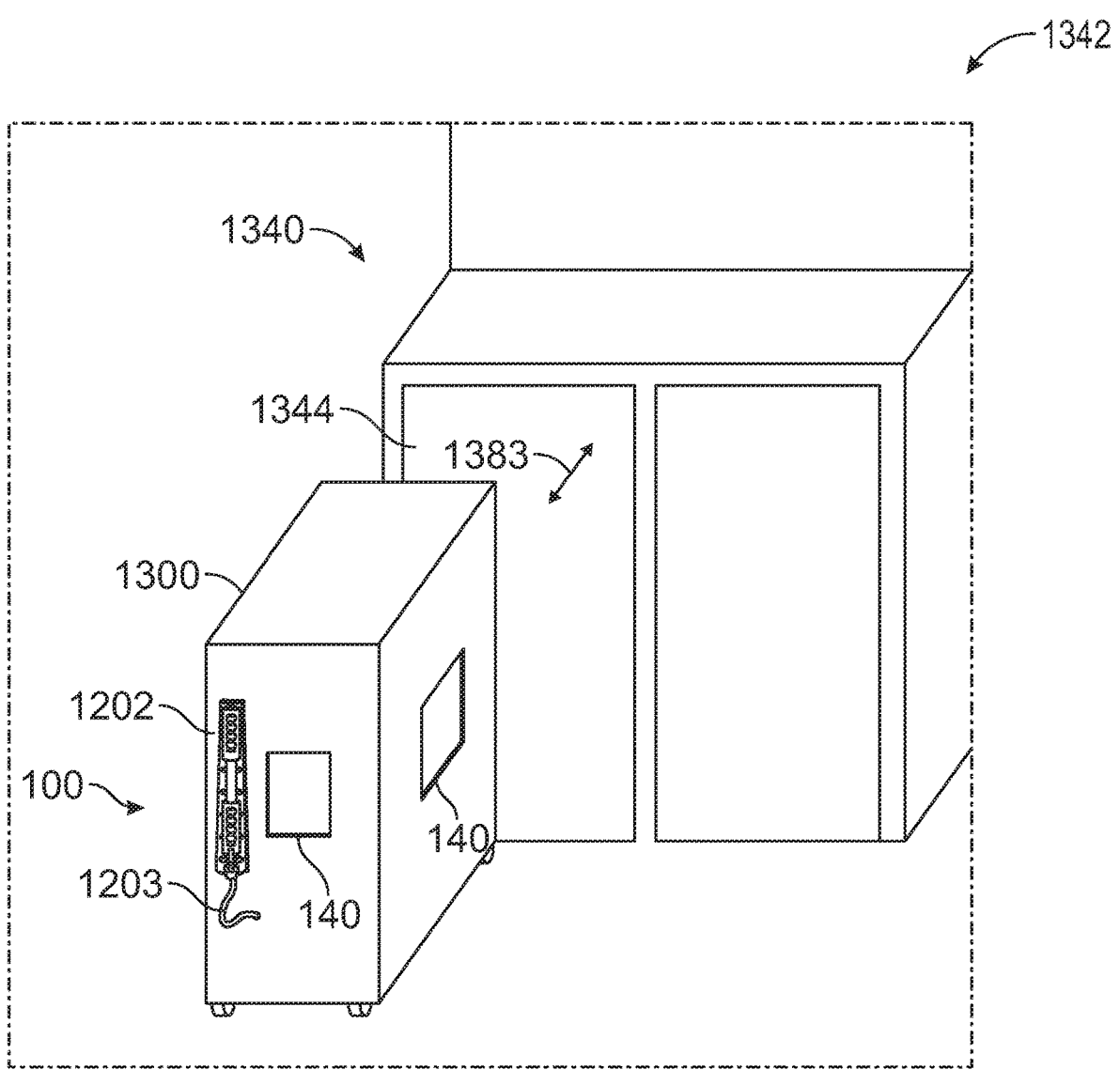
FIG. 38 illustrates a perspective view of a galley within an internal cabin, according to an example of the subject disclosure.

FIG. 38 illustrates a perspective view of a galley 1340 within an internal cabin 1342 (such as the internal cabin 102, shown in FIG. 1), according to an embodiment of the subject disclosure. The galley 1340 includes one or more cart compartments 1344. A cart compartment 1344 is configured to receive and retain the galley cart 1300. For example, the galley cart 1300 is configured to be moved into and out of the cart compartment 1344 in the direction of arrows 1383.

In at least one example, the galley cart 1300 provides the UV light sanitation cart 100. For example, the galley cart

1300 includes one or more UV light sources, such as one or more UV lamps 140, which can be fixed or moveable relative to the galley cart 1300. The galley cart 1300 also includes the wand assembly 1202 connected to the galley cart 1300 through the tether 1203.

FIG. 39 illustrates a flow chart of a UV light sanitizing method, according to an example of the subject disclosure. The UV light sanitizing method includes providing, at 1400, one or more first UV lamps on or within a UV light sanitizing cart; providing, at 1402, one or more wand assemblies comprising one or more second UV lamps on or within the UV light sanitizing cart; and moving, at 1404, the one or more wand assemblies between a stowed position and a deployed position.

In at least one example, said providing the one or more first UV lamps includes securing the one or more first UV lamps to one or more portions of a body of the UV light sanitizing cart. Further, in at least one example, said securing comprises connecting the one or more wand assemblies to the body through one or more tethers. The one or more tethers can include one or more of a power cord, a cable, or an air hose.

In at least one example, the UV light sanitizing method further includes moving the UV light sanitizing cart moved into and out of a compartment within a galley of an internal cabin of a vehicle.

In at least one example, said providing the one or more wand assemblies comprises providing a first wand assembly and a second wand assembly.

Referring to FIGS. 1-39, examples of the subject disclosure provide autonomous or semi-autonomous mobile UV sanitizing equipment that can consistently and efficiently disinfect structures and areas as the equipment moves.

Further, the disclosure comprises embodiments according to the following clauses:

Clause 1: An ultraviolet (UV) light sanitizing cart comprising:

> one or more first UV lamps configured to emit UV light; and
>
> one or more wand assemblies comprising one or more second UV lamps configured to emit UV light,
>
> wherein the one or more wand assemblies are moveable between a stowed position and a deployed position.

Clause 2. The UV light sanitizing cart of Clause 1, further comprising a body having a mobile base, wherein the one or more first UV lamps are secured to one or more portions of the body.

Clause 3. The UV light sanitizing cart of Clause 2, wherein the one or more wand assemblies are connected to the body through one or more tethers.

Clause 4. The UV light sanitizing cart of Clause 3, wherein the one or more tethers comprise one or more of a power cord, a cable, or an air hose.

Clause 5. The UV light sanitizing cart of any of Clauses 1-4, wherein the UV light sanitizing cart is a galley cart configured to be moved into and out of a compartment within a galley of an internal cabin of a vehicle.

Clause 6. The UV light sanitizing cart of any of Clauses 1-5, wherein the one or more first UV lamps and the one or more second UV lamps are configured to emit the UV light at a wavelength within the far UV spectrum.

Clause 7. The UV light sanitizing cart of any of Clauses 1-6, wherein the one or more first UV lamps and the one or more second UV lamps are configured to emit the UV light at a wavelength of 222.

Clause 8. The UV light sanitizing cart of any of Clauses 1-6, wherein the one or more first UV lamps and the one or more second UV lamps are configured to emit the UV light at a wavelength within the UVC spectrum.

Clause 9. The UV light sanitizing cart of any of Clauses 1-6, wherein the one or more first UV lamps and the one or more second UV lamps are configured to emit the UV light at a wavelength of 254.

Clause 10. The UV light sanitizing cart of any of Clauses 1-9, wherein the one or more wand assemblies comprise a first wand assembly and a second wand assembly.

Clause 11. The UV light sanitizing cart of any of Clauses 1-10, wherein the one or more wand assemblies comprise:

> a handle; and
>
> a sanitizing head coupled to the handle, wherein the sanitizing head comprises the one or more second UV lamps.

Clause 12. The UV light sanitizing cart of Clause 11, wherein the sanitizing head is moveably coupled to the handle.

Clause 13. An ultraviolet (UV) light sanitizing method comprising:

> providing one or more first UV lamps on or within a UV light sanitizing cart;
>
> providing one or more wand assemblies comprising one or more second UV lamps on or within the UV light sanitizing cart; and
>
> moving the one or more wand assemblies between a stowed position and a deployed position.

Clause 14. The UV light sanitizing method of Clause 13, wherein said providing the one or more first UV lamps comprises securing the one or more first UV lamps to one or more portions of a body of the UV light sanitizing cart.

Clause 15. The UV light sanitizing method of Clause 14, wherein said securing comprises connecting the one or more wand assemblies to the body through one or more tethers.

Clause 16. The UV light sanitizing method of Clause 15, wherein the one or more tethers comprise one or more of a power cord, a cable, or an air hose.

Clause 17. The UV light sanitizing method of any of Clauses 13-16, further comprising moving the UV light sanitizing cart moved into and out of a compartment within a galley of an internal cabin of a vehicle.

Clause 18. The UV light sanitizing method of any of Clauses 13-17, wherein the one or more first UV lamps and the one or more second UV lamps are configured to emit the UV light at a wavelength within the far UV spectrum.

Clause 19. The UV light sanitizing method of any of Clauses 13-18, wherein the one or more first UV lamps and the one or more second UV lamps are configured to emit the UV light at a wavelength of 222.

Clause 20. The UV light sanitizing method of any of Clauses 13-17, wherein the one or more first UV lamps and the one or more second UV lamps are configured to emit the UV light at a wavelength within the UVC spectrum.

Clause 21. The UV light sanitizing method of any of Clauses 13-17, wherein the one or more first UV lamps and the one or more second UV lamps are configured to emit the UV light at a wavelength of 254.

Clause 22. The UV light sanitizing method of any of Clauses 13-21, wherein said providing the one or more wand assemblies comprises providing a first wand assembly and a second wand assembly.

Clause 23. An ultraviolet (UV) light sanitizing cart comprising:

> a body having a mobile base;
>
> one or more first UV lamps secured to one or more portions of the body, wherein the one or more first UV lamps are configured to emit UV light; and one or more wand assemblies comprising one or more second UV lamps configured to emit UV light, wherein the one or more wand assemblies are connected to the body through one or more tethers, wherein the one or more wand assemblies are moveable between a stowed position and a deployed position, and wherein the one or more first UV lamps and the one or more second UV lamps are configured to emit the UV light at a wavelength within the far UV spectrum.

Clause 24. The UV light sanitizing cart of Clause 23, wherein the one or more wand assemblies comprise:

a handle; and a sanitizing head moveably coupled to the handle, wherein the sanitizing head comprises the one or more second UV lamps.

While various spatial and directional terms, such as top, bottom, lower, mid, lateral, horizontal, vertical, front and the like can be used to describe examples of the subject disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described examples (and/or aspects thereof) can be used in combination with each other. In addition, many modifications can be made to adapt a particular situation or material to the teachings of the various examples of the disclosure without departing from their scope. While the dimensions and types of materials described herein are intended to define the parameters of the various examples of the disclosure, the examples are by no means limiting and are exemplary examples. Many other examples will be apparent to those of skill in the art upon reviewing the above description. The scope of the various examples of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various examples of the disclosure, including the best mode, and also to enable any person skilled in the art to practice the various examples of the disclosure, including making and using any devices or systems and performing any incorporated methods. The patentable scope of the various examples of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system comprising:

a galley cart including:

one or more first UV lamps configured to emit UV light, wherein the one or more first UV lamps are secured to one or more arms that are movable between an extended position and a retracted position;

one or more recesses formed in one or more exterior surfaces; and one or more wand assemblies comprising one or more second UV lamps configured to emit UV light, wherein the one or more recesses conform to an outer surface of at least a portion of the one or more wand assemblies, and wherein the one or more wand assemblies are moveable between a stowed position and a deployed position, wherein the outer surface of the at least a portion of the one or more wand assemblies is retained within the one or more recesses in the stowed position, and wherein the one or more wand assemblies are removed from the one or more recesses in the deployed position.

2. The system of claim 1, wherein the one or more first UV arms retaining the one or more first UV lamps are secured to one or more portions of the galley cart.

3. The system of claim 2, wherein the one or more wand assemblies are connected to the galley cart through one or more tethers.

4. The system of claim 3, wherein the one or more tethers comprise one or more of a power cord, a cable, or an air hose.

5. The system of claim 1, wherein the one or more first UV lamps and the one or more second UV lamps are configured to emit the UV light at a wavelength within the far UV spectrum.

6. The system of claim 1, wherein the one or more first UV lamps and the one or more second UV lamps are configured to emit the UV light at a wavelength of 222 nm.

7. The system of claim 1, wherein the one or more first UV lamps and the one or more second UV lamps are configured to emit the UV light at a wavelength within the UVC spectrum.

8. The system of claim 1, wherein the one or more first UV lamps and the one or more second UV lamps are configured to emit the UV light at a wavelength of 254 nm.

9. The system of claim 1, wherein the one or more wand assemblies comprise a first wand assembly and a second wand assembly.

10. The system of claim 1, wherein the one or more wand assemblies comprise:

a handle; and a sanitizing head coupled to the handle, wherein the sanitizing head comprises the one or more second UV lamps.

11. The system of claim 10, wherein the sanitizing head is moveably coupled to the handle.

12. The system of claim 1, further comprising a galley within an internal cabin of a vehicle, the galley including compartments, wherein the galley cart is moveable into and out of one or more of the compartments.

13. An ultraviolet (UV) light sanitizing method comprising:

provinding one or more first UV lamps on or within a galley cart, wherein the one or more first UV lamps are secured to one or more arms;

moving the one or more arms between an extended position and a retracted position;

providing one or more wand assemblies comprising one or more second UV lamps on or within the galley cart; and moving the one or more wand assemblies between a stowed position and a deployed position, wherein the galley cart comprises one or more recesses formed in one or more exterior surfaces, wherein the one or more recesses conform to an outer surface of at least a portion of the one or more wand assemblies, wherein the outer surface of the at least a portion of the one or more wand assemblies is retained within the one or more recesses in the stowed position, and wherein the one or more wand assemblies are removed from the one or more recesses in the deployed position.

14. The UV light sanitizing method of claim 13, wherein said providing the one or more first UV lamps comprises securing the one or more first UV lamps to one or more portions of the galley cart.

15. The UV light sanitizing method of claim 14, wherein said securing comprises connecting the one or more wand assemblies to the body through one or more tethers.

16. The UV light sanitizing method of claim 15, wherein the one or more tethers comprise one or more of a power cord, a cable, or an air hose.

17. The UV light sanitizing method of claim 13, further comprising moving the galley cart into and out of a compartment within a galley of an internal cabin of a vehicle.

18. The UV light sanitizing method of claim 13, wherein the one or more first UV lamps and the one or more second UV lamps are configured to emit the UV light at a wavelength within the far UV spectrum.

19. The UV light sanitizing method of claim 13, wherein the one or more first UV lamps and the one or more second UV lamps are configured to emit the UV light at a wavelength of 222 nm.

20. The UV light sanitizing method of claim 13, wherein the one or more first UV lamps and the one or more second UV lamps are configured to emit the UV light at a wavelength within the UVC spectrum.

21. The UV light sanitizing method of claim 13, wherein the one or more first UV lamps and the one or more second UV lamps are configured to emit the UV light at a wavelength of 254 nm.

22. The UV light sanitizing method of claim 13, wherein said providing the one or more wand assemblies comprises providing a first wand assembly and a second wand assembly.

23. A vehicle comprising:

an internal cabin having a galley, wherein the galley includes compartments;

a system comprising:

a galley cart having a mobile base, and one or more recesses formed in one or more exterior surfaces;

one or more first UV lamps secured to one or more portions of the galley cart, wherein the one or more first UV lamps are configured to emit UV light, and wherein the one or more first UV lamps are secured to one or more arms that are movable between an extended position and a retracted position; and one or more wand assemblies comprising one or more second UV lamps configured to emit UV light, wherein the one or more wand assemblies are connected to the galley cart through one or more tethers, wherein the one or more recesses conform to an outer surface of at least a portion of the one or more wand assemblies, wherein the one or more wand assemblies are moveable between a stowed position and a deployed position, wherein the outer surface of the at least a portion of the one or more wand assemblies is retained within the one or more recesses in the stowed position, wherein the one or more wand assemblies are removed from the one or more recesses in the deployed position, wherein the one or more first UV lamps and the one or more second UV lamps are configured to emit the UV light at a wavelength within the far UV spectrum, and wherein the galley cart is moveable into and out of one or more of the compartments of the galley within the internal cabin.

24. The vehicle of claim 23, wherein the one or more wand assemblies comprise:

a handle; and a sanitizing head moveably coupled to the handle, wherein the sanitizing head comprises the one or more second UV lamps.

* * * * *